United States Patent [19]

Bagli et al.

[11] 4,054,741

[45] Oct. 18, 1977

[54] DERIVATIVES OF PROSTANOIC ACID

[75] Inventors: Jehan F. Bagli, Valois Gardens; Tibor Bogri, Montreal, both of Canada

[73] Assignee: Ayerst McKenna & Harrison Ltd., Montreal, Canada

[21] Appl. No.: 697,901

[22] Filed: June 21, 1976

Related U.S. Application Data

[60] Division of Ser. No. 591,231, June 27, 1975, abandoned, which is a division of Ser. No. 377,973, July 5, 1973, Pat. No. 3,907,998, which is a continuation of Ser. No. 259,876, June 5, 1972, Pat. No. 3,773,795, which is a continuation-in-part of Ser. No. 157,704, June 28, 1971, abandoned.

[51] Int. Cl.$^2$ ............................................ C07C 177/00
[52] U.S. Cl. ................................ 560/121; 260/514 D
[58] Field of Search ........................ 260/468 D, 514 D

[56] References Cited

U.S. PATENT DOCUMENTS 3,671,570  6/1972  Bagli et al. ............................ 260/468

*Primary Examiner*—Robert Gerstl
*Attorney, Agent, or Firm*—Adley F. Mandel

[57] ABSTRACT

Process for preparing prostanoic acid derivatives, in particular derivatives of 9,15-dioxygenated prostanoic acid and prost-13-enoic acid, related additionally unsaturated derivatives, homologs thereof and intermediates therefor, in which a lower alkyl ester of 2-(ω-carboxy-Y)cyclopent-2-en-1-one in which Y is $CH_2$—(a)—$(CH_2)_m$ wherein (a) is $CH_2CH_2$, CH=CH or C≡C and $m$ is an integer from 2 – 4 is treated with nitromethane to yield 2-(ω-carboxy-Y)-3-nitromethyl-cyclopentan-1-one and the latter compound or its corresponding 1-hydroxy analog are converted to the corresponding aldehyde, 2-(ω-carboxy-Y)cyclopentan-1-on-3-al or 1-hydroxy-2-(ω-carboxy-Y)cyclopentan-3-al, respectively. Treatment of the aldehyde with the ylid prepared from the appropriate Wittig reagent, preferably a dimethyl 2-oxoalkylphosphonate of the formula (AlkO)$_2$P(O)CH$_2$CO(CH$_2$)$_n$CH$_3$ in which $n$ is an integer of from 1-6 and Alk is an alkyl containing from 1 – 3 carbon atoms yields the corresponding derivatives of 2-(ω-carboxy-Y)-3-(3-oxoalk-1-enyl)cyclopentan-1-one or -1-ol in which the oxygen functions may be selectively protected and transformed by conventional means, and in which the unsaturated bonds may be reduced to a single bond. The prostanoic acid derivatives possess prostaglandin like biological activities. Methods for their use are also disclosed.

3 Claims, No Drawings

DERIVATIVES OF PROSTANOIC ACID

This is a division, of application Ser. No. 591,231, filed June 27, 1975, now abandoned which is a division of Ser. No. 377,973 filed July 5, 1973, now U.S. Pat. No. 3,907,998, which is a continuation of Ser. No. 259,876 filed June 5, 1972 now U.S. Pat. No. 3,773,795 which is a continuation-in-part of Ser. No. 157,704 filed June 28, 1971 which is now abandoned.

BACKGROUND OF THE INVENTION

This invention relates to a process for preparing derivatives of prostanoic acid, in particular 9,15-dioxygenated derivatives of prostanoic acid and prost-13-enoic acid, related additionally unsaturated derivatives, to homologs thereof, and to intermediates used in their preparation.

The preparation of derivatives of prostanoic acid has become of great importance since the demonstration of the highly interesting biological activities of the natural prostaglandins, see e.g. Bergstrom, Abstracts International Congress of Biochemistry, Vol. 7, p. 559 (1964). Several synthetic methods for the preparation of 9,15-dioxygenated derivatives of prostanoic or prost-13-enoic acids have been described. For example, Bagli and Bogri in U.S. Pat. No. 3,432,541 issued Mar. 11, 1969, have described a 14-step process for preparing 9$\zeta$,15$\zeta$-dihydroxyprost-13-enoic acid (11-desoxyprostaglandin F$_1$) from cyclopentanone ethyl carboxylate and ethyl bromoheptanoate in which the unsaturated side chain was built up stepwise from the corresponding 3-carboxylic acid chloride. A significant simplification of that process was described by Bagli and Bogri in U.S. Pat. No. 3,455,992 issued July 15, 1969, in which the unsaturated side chain was introduced by reaction of the chloride of 2-(6-carbomethoxyhexyl)cyclopentan-1-one-3-carboxylic acid, obtained as described in U.S. Pat. No. 3,432,541, with the appropriate alkyne to obtain the corresponding unsaturated chloroketone, from which 9$\zeta$,15$\zeta$-dihydroxyprost-13-enoic acid as well as homologs thereof are obtained by transformation of the chloro substituent to an oxygen function and removal of the keto group with concomitant dehydration.

A further improvement in the synthesis of 9,15-dioxygenated derivatives of prostanoic acid has been described by Bagli and Bogri in Tetrabedron Letters 1639 (1969). The oxygen-containing side-chain was introduced by treating 2-(6-carbomethoxyhexyl)cyclopent-2-en-1-one, prepared as described in U.S. Pat. No. 3,432,541, with an alkyl chlorovinyl ketone, with irradiation by means of a mercury vapour lamp, to obtain the intermediate 7-alkanoyl-6-chloro-2-oxobicyclo[3,2,0]-heptane-1-heptanoic acid methyl ester. Treatment of the latter compound with zinc and acetic acid gave 9,15-dioxoprostanoic acid methyl ester and homologs thereof, from which a number of other 9,15-dioxygenated derivatives of prostanoic acid and of homologs thereof were prepared by conventional means. It should be noted that this method permits only the obtention of compounds with a saturated oxygen-containing side-chain. However, it is particularly noteworthy that in all the processes described above the acidic side-chain and the oxygen-containing side-chain are in the trans configuration characteristic for the natural prostaglandins, and that the synthetic compounds described above possess a number of the biological activities of the natural compounds although they lack the 11-hydroxy group of the latter.

Other synthetic processes in this field have been summarized by Axen and Smissman, and by Bagli, in Annual Reports in Medicinal Chemistry, 290 (1967) and 170 (1969), respectively. While some of those processes have been useful in the laboratory, none of them have so far gained industrial importance. It is the object of this invention to provide a simple, economical and efficient process for the synthesis of 9,15-dioxygenated derivatives of prostanoic or prost-13-enoic acids, related additionaly unsaturated derivatives and homologs thereof which permits their preparation on a large scale.

In the following the terms "lower alkyl" will denote straight or branched alkyl groups containing from 1 – 3 carbon atoms and straight alkyl chains containing from 4–6 carbon atoms and include methyl, ethyl, propyl, isopropyl, butyl, pentyl, and hexyl; in accordance with the definition of $n$ as an integer of from 1–6, the terms "3-oxoalk-1-enyl", "3-oxoalk-1-yl", "3-hydroxyalk-1-enyl" and "3-hydroxyalk-1-yl" denote straight alkyl or alkenyl chains substituted with the appropriate oxygen function in position 3 and containing from 5–10 carbon atoms, the term "2-oxoalkyl" used in connection with the Wittig reagent denotes straight alkyl chains having a ketonic oxygen in position 2 and containing from 4–9 carbon atoms, and the term "tetrahydropyranyl" will denote a tetrahydropyran-2-yl radical.

In the following the symbol Y as used herein represents a divalent radical of formula $CH_2$—(a)—$(CH_2)_m$ in which (a) is $CH_2CH_2$, $CH=CH$ or $C\equiv C$ and $n$ is an integer from 2 – 4 carbon atoms.

SUMMARY OF THE INVENTION

In practicing the process of this invention, a lower alkyl ester of 2-($\omega$-carboxy-Y)cyclopent-2-en-1-one (I, R = lower alkyl, preferably the methyl ester, conveniently prepared by treating a 2-($\omega$-carboxy-Y)cyclopent-2-en-1-one, see below, with a lower alkanol containing from 1 – 6 carbon atoms and p-toluenesulfonic acid, is treated with nitromethane in the presence of an alkali metal lower alkoxide, preferably sodium methoxide, to yield the corresponding lower alkyl ester, preferably the methyl ester, of a 2-($\omega$-carboxy-Y)-3-nitromethyl-cyclopentan-1-one (II, R = lower alkyl) which may be treated with an alkali metal hydroxide, preferably sodium hydroxide, to yield the corresponding free acid (II, R = H). This addition takes place exclusively in the $\beta$-position, with no carbonyl addition product being formed, and although a somewhat similar addition reaction is known to take place with cyclohexenone (see McCoubrey, J. Chem. Soc. 1951, 2931), the highly specific $\beta$-addition described above does not seem to be known in the cyclopentene series.

The 1-keto group of th6-($\omega$-carboxy-Y)-3-nitromethyl-cyclopentan-1-one (II, R = H) or of a lower alkyl ester thereof (II, R = lower alkyl) may be reduced by treatment with an alkali metal borohydride, preferably sodium borohydride, to yield the corresponding 2-($\omega$-carboxy-Y)-3-nitromethyl-cyclopentan-1-ol (III, R = H) or the corresponding lower alkyl ester thereof (III, R = lower alkyl), respectively.

The nitromethyl derivatives of formulae II or III described above are converted to their respective aci-forms by treatment with a strong base such as an alkali metal lower alkoxide, preferably sodium methoxide, or an aqueous alkali metal hydroxide, preferably sodium hydroxide, and the resulting solution of the alkali metal salt of the corresponding nitronic acid is added to a cold aqueous solution of a mineral acid, preferably dilute sulfuric acid at a temperature in the range between about −10° C. and about 25° C., preferably in the vicinity of 0° C. Extraction of the mixture with a water-immiscible solvent, preferably diethyl ether, and evaporation of the latter yields the corresponding 3-aldehyde. When the starting material for this reaction is being used in the form of its lower alkyl ester (II or III, R = lower alkyl) and an alkali metal alkoxide is used to generate the salt of the corresponding nitronic acid, the corresponding lower alkyl ester of 2-(ω-carboxy-Y)cyclopentan-1-on-3-al (IV, R = lower alkyl) or of 2-(ω-carboxy-Y)cyclopentan-1-ol-3-al (V, R = lower alkyl), is obtained; and when an alkali metal hydroxide is being used to generate the salt of the corresponding nitronic acid, or when the starting material is the free acid (II or III, R = H), 2-(ω-carboxy-Y)cyclopentan-1-on-3-al (IV, R = H) or 2-(ω-carboxy-Y)cyclopentan-1-ol-3-al (V, R = R$^1$ = H) is obtained.

In a variant of the above procedure, 2-(ω-carboxy-Y)-cyclopentan-1-on-3-al (IV, R = H) or a lower alkyl ester thereof (IV, R = lower alkyl) is converted to the corresponding lower alkyl ester di(lower alkyl) acetal (VI, R = lower alkyl) by treatment with a lower alkanol, preferably methanol, in the presence of an acid catalyst. Suitable acid catalysts are mineral acids such as hydrochloric, hydrobromic, phosphoric, or sulfuric acids; organic acids such as trifluoroacetic or p-toluenesulfonic acids; Lewis acids such as boron trifluoride; or acidic ion exchange resins. The preferred catalyst is p-toluenesulfonic acid. The starting material need not be purified for this reaction, and the crude 3-aldehyde obtained as described above may be used. The di(lower alkyl) acetal (VI, R = lower alkyl) obtained above is treated with an alkali metal borohydride, preferably sodium borohydride, to yield the corresponding di(-lower alkyl) acetal in which the 1-keto group has been replaced by the 1-hydroxy group (VII, R = lower alkyl), and treatment of the latter compound with an acid preferably a dilute mineral acid, yields the corresponding 3-aldehyde (V, R = lower alkyl, R$^1$ = H) described above.

In the following sequence of reactions it is preferred to use one of the lower alkyl esters, preferably the methyl ester, of 2-(ω-carboxy-Y)cyclopentan-1-on-3-al (IV, R = lower alkyl) or of 2-(ω-carboxy-Y)cyclopentan-1-ol-3-al (V, R = lower alkyl and R$^1$ = H) rather than the corresponding free acid as the starting material, as the subsequent compounds containing free carboxylic acid group are somewhat more difficult to purify. However, it is understood that the free acids of formulae IV or V in which R is hydrogen are also useful as starting materials.

In the preferred form of the process of this invention, a lower alkyl ester of 2-(ω-carboxy-Y) cyclopentan-1-on-3-al (IV, R = lower alkyl) is treated at 25°–85° C with the ylid prepared from a Wittig reagent of the formula (AlkO)$_2$P(O)CH$_2$CO(CH$_2$)$_n$CH$_3$ in which $n$ is an integer of from 1–6 and Alk is an alkyl containing from 1–3 carbon atoms, preferably a dimethyl 2-oxoalkylphosphonate, in the presence of an alkali metal hydride, preferably sodium hydride, and in an aprotic solvent, preferably dimethoxyethane. Acidification with an aqueous acid, preferably aqueous hydrochloric acid, extraction with a water-immiscible solvent, preferably diethyl ether, followed by washing, drying and evaporation of the latter, yields the corresponding lower alkyl ester of a 2-(ω-carboxy-Y)-3-(3-oxoalk-1-enyl)-cyclopentan-1-one of formula VIII in which R is lower alkyl and $n$ is as defined above.

If desired the latter compound or its corresponding acid in which R is hydrogen is reduced with an alkali metal borohydride, preferably sodium borohydride, to yield the corresponding lower alkyl ester of a 2-(ω-carboxy-Y)-3-(3-hydroxyalk-1-enyl)cyclopentan-1-one of formula VIIIa. Alkaline hydrolysis of the latter compounds yields the corresponding acid (VIIIa, R = H).

On the other hand the compound of formula VIII in which R is lower alkyl and $n$ is as defined above may be treated with ethylene glycol in the presence of a catalytic amount of p-toluenesulfonic acid, to yield the corresponding ethylene ketal, a lower alkyl ester of a 2-(ω-carboxy-Y)-3-(3-oxoalk-1-enyl)-cyclopentan-1-one ethylene ketal of formula IX in which R is lower alkyl and $n$ is as defined above. The crude ethylene ketal obtained as described above, without further purification, is treated with an alkali metal borohydride in solution in a lower alkanol, preferably sodium borohydride in methanol, followed by evaporation of the solvent and extraction with a water-immiscible solvent, preferably diethyl ether, followed by evaporation of the latter, to yield the corresponding lower alkyl ester of a 2-(ω-carboxy-Y)-3-(3-hydroxyalk-1-enyl)-cyclopentan-1-one ethylene ketal of formula X in which R is lower alkyl and $n$ is as defined above. Treatment of said last-named compound with an aqueous acid, preferably p-toluenesulfonic acid in a mixture of a lower alkanol such as methanol and water, yields the corresponding lower alkyl ester of a 2-(ω-carboxy-Y)-3-(3-hydroxyalk-1-enyl)-cyclopentan-1-one of formula XI in which R is lower alkyl and $n$ is as defined above.

When the starting material of formula IV used in the above sequence of reactions is the methyl ester of 2-(6-carboxyhexyl)cyclopentan-1-on-3-al and the Wittig reagent employed is dimethyl 2-oxoheptyl-phosphonate of the formula (MeO)$_2$P(O)CH$_2$CO(CH$_2$)$_n$CH$_3$ in which $n$ = 4, the compound of the formula VIII in which Y is CH$_2$–(a)—(CH$_2$)$_m$ wherein (a) is CH$_2$CH$_2$ and $n$ = 3, R is methyl and $n$ = 4 obtained is 9,15-dioxoprost-13-enoic acid methyl ester, which may be reduced by treatment with hydrogen and a noble metal catalyst, preferably palladium on charcoal, to the corresponding 9,15-dioxoprostanoic acid methyl ester, identical with the same compound described in French patent application No. 2,021,234, published July 17, 1970. The compound of formula VIIIa in which Y is CH$_2$—(a)—(CH$_2$)$_m$ wherein (a) is CH$_2$CH$_2$ and $m$ = 3, R is methyl and $n$ = 4 obtained from the latter compound of formula VIII is 9ε,15ε-dihydroxyprost-13-enoic acid methyl ester, identical with the same compound described in U.S. Pat. No. 3,432,541 as cited above. The compound of formula IX in which Y is CH$_2$—(a)—(CH$_2$)$_m$ wherein (a) is CH$_2$CH$_2$ and $m$ = 3, R is methyl and $n$ = 4 obtained from the latter compound of formula VIII is 9-ethylene-dioxy-15-oxoprost-13-enoic acid methyl ester; the compound of formula X in which Y is CH$_2$—(a)—(CH$_2$)$_m$ wherein (a) is CH$_2$CH$_2$ and $m$ = 3, R is methyl and $n$ = 4 obtained therefrom is 9-ethylenedioxy-15-hydroxyprost-13-enoic acid methyl ester; and the compound of formula XI in which Y is CH$_2$—(a)—(CH$_2$)$_m$ wherein (a) is CH$_2$CH$_2$ and $m$ = 3, R is methyl and $n$ = 4 is 15-hydroxy-9-oxoprost-13-enoic acid methyl ester, identical with the same compound described in British Pat. No. 1,218,998, published Jan. 13, 1971, which may be reduced by treatment with hydrogen and a noble metal catalyst, preferably palladium on charcoal, to 9-oxo-15- hydroxyprostanoic methyl ester, identical with the same compound described in French patent application No. 2,021,234, published July 17, 1970.

As another alternative of the above preferred procedure, a lower alkyl ester of 2-(ω-carboxy-Y)cyclopentan-1-ol-3-al of formula V in which R is lower alkyl and $R^1$ is hydrogen, is treated with dihydropyran in the presence of an acid catalyst as exemplified above, preferably p-toluenesulfonic acid, to yield the corresponding lower alkyl ester of 1-tetrahydropyranyloxy-2-(ω-carboxy-Y)cyclopentan-1-al (V, R = lower alkyl, $R^1$ = tetrahydropyranyl). Treatment of said last-named compound at 25° – 85° C, preferably at about 60° – 65° C, with the ylid prepared from a Wittig reagent of the formula $(AlkO)_2P(O)CH_2CO(CH_2)_nCH_3$ in which $n$ is an integer of from 1 – 6 and Alk is an alkyl containing from 1 – 3 carbon atoms, preferably a dimethyl 2-oxoalkylphosphonate, in the presence of an alkali metal hydride, preferably sodium hydride and in an aprotic solvent, preferably dimethoxyethane, followed by treatment with a weak acid, preferably aqueous acetic acid, yields the corresponding lower alkyl ester of a 2-(ω-carboxy-Y)-3-(3-oxoalk-1-enyl)-cyclopentan-1-ol tetrahydropyranyl ether of the formula XII in which R is lower alkyl and $R^1$ is tetrahydropyranyl, respectively.

In a related aspect of this invention the last-named compound is treated with an alkali metal borohydride, preferably sodium borohydride, in the same manner as described above to give the corresponding 3-hydroxyalk-1-enyl compound which on acid hydrolysis, for example, hydrolysis with p-toluenesulfonic acid, trifluoroacetic acid or acetic acid in aqueous methanol, yields the corresponding lower alkyl ester of 2-(ω-carboxy-Y)-3-(3-hydroxyalk-1-enyl)cyclopentan-1-one of formula VIIIa (R = lower alkyl). Again, if desired, alkaline hydrolysis of the latter compound yields the corresponding acid (VIIIa, R = H).

When the Wittig reagent used in the above reaction is dimethyl 2-oxoheptylphosphonate and the compound of formula V is the methyl ester of 1-tetrahydropyranyloxy-2-(6-carboxyhexyl)cyclopentan-1-al the compound obtained is the tetrahydropyranyl ether of 9-hydroxy-15-oxoprost-13-enoic acid methyl ester (XII; Y = $(CH_2)_6$, R = $CH_3$, $R^1$ = tetrahydropyranyl, $n$ = 4), identical with the same compound described in British Pat. No. 1,218,998, published Jan. 13, 1971. Treatment of said last-named compound with sodium borohydride gives the corresponding 15-hydroxy derivative, which is acylated at position 15, the protective ether group removed from position 9 to give the corresponding 9-hydroxy-15-acyloxy derivative, which upon treatment with chromic acid in acetone followed by removal of the protective acyl group at position 15, all in the manner described in British Pat. No. 1,218,998 cited above, yields 15-hydroxy-9-oxoprost-13-enoic acid methyl ester of formula XI in which Y = $(CH_2)_6$, R is methyl and $n$ = 4.

The above compounds of formula XI may be treated with hydrogen in the presence of a moble metal catalyst to yield the corresponding lower alkyl esters of a 2-(ω-carboxy-Y)-3-(3-hydroxyalk-1-yl)-cyclopentan-1-one in which Y is $CH_2$—(a)—$(CH_2)_m$ wherein (a) is $CH_2CH_2$ and $m$ = 2 to 4, of which 9-oxo-15-hydroxyprostanoic acid has been described in French patent application No. 2,021,234, cited above. Further treatment of said last-named compounds with an alkali metal borohydride, preferably sodium borohydride, yields the corresponding lower alkyl esters of a 2-(ω-carboxy-Y)-3-(3-hydroxyalk-1-yl))-cyclopentan-1α-ol or 1β-ol, in which Y is $CH_2$—(a)—$(CH_2)_m$ wherein (a) is $CH_2CH_2$ and $m$ = 2 – 4, of which 9α,15ζ- and 9β,15ζ-dihydroxyprostanoic acid methyl ester are also described in French patent application No. 2,021,234 cited above. The compounds of formula XI may also be reduced with an alkali metal borohydride in the same manner described above to give the corresponding diol compounds of formula VIIIa, described above.

The compounds of this invention, namely the compounds of formula XI, and their products of reduction, namely the compounds of formulae VIIIa, XIII and XIV, possess interesting pharmacological properties when tested in standard pharmcological tests. In particular, they have been fond to possess hypotensive, antihypertensive, bronchospasmolytic, and gastric acid secretion inhibiting properties, which make them useful in the treatment of conditions associated with high blood pressure, in the treatment of asthmatic conditions and in the treatment of pathological conditions associated with excessive scretion of gastric acid such as, for example peptic ulcer. In addition, the compounds of this invention inhibit the aggregation of platelets and promote the disaggregation of aggregated platelets, and are useful as agents for the prevention and treatment of thrombosis.

More particularly, these compounds, when tested in a modification of the tests for determining hypotensive activities described in "Screening Methods in Pharmacology", Academic Press, New York and London 1965, page 146, using the cat in urethane-chloralose anaesthesia as the test animal and measuring mean arterial blood pressure before and after intravenous administration of the compounds, have exhibited utility as hypotensive agents. When tested in the renal hypertensive rat prepared by the method of A. Grollman described in Proc. Soc. Exp. Biol. Med., Vol. 7, p. 102 (1954), and measuring blood pressure by the method described by H. Kersten in J. Lab. Clin. Med., Vol. 32, p. 1090 (1947), they have exhibited utility as antihypertensive agents.

Furthermore, the compounds of this invention, when administered to rats in the test method described by Shay et al. Gastrecenterology, Vol. 26, p. 906 (1954), have been found to inhibit the secretion of gastric acid, and are useful as agents inhibiting the secretion of gastric acid.

Moreover, the compounds of this invention, when tested in a modification of the test method described by Armitage et al. in Brit. J. Pharmacol., Vol. 16, p. 59 (1961), have been found to alleviate bronchospasms, and are useful as bronchospasmolytic agents.

In addition, the compounds of this invention, when tested in a modification of the test method described by G.V.R. Born in Nature, Vol. 194, p. 927 (1962), using the aggregometer manufactured by Bryston Manufacturing Limited, Rexdale, Ontario, Canada, have been shown to inhibit the aggregation of platelets and to promote the disaggregation of aggregated platelets, and are useful as agents for the prevention and treatment of thrombosis.

When the compounds of this invention are employed as hypotensive or anti-hypertensive agents, as agents inhibiting gastric acid secretion in warm-blooded animals, for example, in cats or rats, as agents for the prevention or treatment of thrombosis, or as bronchospasmolytic agents, alone or in combination with pharmacologically acceptable carriers, their proportions are determined by their solubilities, by the chosen route of administration, and by standard biological practice. The compounds of this invention may be administered orally in solid form containing such excipients as starch, lactose, sucrose, certain types of clay, and flavouring and coating agents. However, they are preferably administered parenterally in the form of sterile solutions thereof which may also contain other solutes, for example, sufficient sodium chloride or glucose to make the solution isotonic. For use as bronchospasmolytic agents, the compounds of this invention are preferably administered as aerosols.

The dosages of the present hypotensive, antihypertensive, gastric acid secretion inhibiting, or bronchospasmolytic agents, or agents for the prevention and treatment of thrombosis will vary with the forms of administration and the particular hosts under treatment. Generally, treatments are initiated with small dosages substantially less than the optimum doses of the compounds. Thereafter, the dosages are increased by small increments until the optimum effects under the circumstances are reached. In general, the compounds of this invention are most desirably administered at a concentration level that will generally afford effective results without causing any harmful or deleterious side effects and preferably at a level that is in a range of from about 0.1mg. to about 10.0 mg. per kilo, although as aforementioned variation will occur. However, a dosage level that is in range of from about 0.5 mg. to about 5 mg. per kilo is most desirably employed in order to achieve effective results. When administering the compounds of this invention as aerosols the liquid to be nebulized contains preferably from 0.005 – 0.05 percent of the active ingredient.

DETAILED DESCRIPTION OF THE INVENTION

More specifically, a solution of a lower alkyl ester of 2-(ω-carboxy-Y)cyclopent-2-en-1-one, (I, R = lower alkyl) preferably the methyl ester, in approximately 1.4 parts of a lower alkanol, preferably methanol, and a solution containing approximately one equivalent of an alkali metal lower alkoxide in the same lower alkanol as above, preferably sodium methoxide in methanol, are both added simultaneously with agitation to a solution of approximately 2.5 equivalents of nitromethane in approximately one part of the same lower alkanol as above, preferably methanol. The temperature during addition is kept somewhat below the boiling point of the mixture, preferably at about 60° C, and after completion of addition the mixture is stirred for two hours at approximately the same temperature. The mixture is cooled, neutralized by addition of 50% acetic acid, the solvent evaporated under reduced pressure, the residue taken up in a water-immiscible solvent, preferably diethyl ether, the extracts washed, dried, and evaporated, and the residue purified by chromatography on silica gel. The corresponding 3-nitromethyl derivative, a lower alkyl ester, preferably the methyl ester, of 2-(ω-carboxy-y)-3-nitromethyl-cyclopentan-1-one (II, R = lower alkyl) is obtained by evaporation of the eluates.

The last-named compound of formula II is treated with a solution of 1-2 equivalents, preferably about 1.5 equivalents, of an alkali metal lower alkoxide in a lower alkanol, preferably sodium methoxide in methanol, at a temperature of from 15°-35° C, preferably at room temperature for a period of time of from 10–60 minutes, preferably for about 30 minutes. The resulting solution of the alkali metal salt of the corresponding nitronic acid is slowly added with stirring over a period of time of from 10–60 minutes, preferably about 25 minutes, to an aqueous solution of a molar excess, preferably about 30 equivalents of a mineral acid, preferably about 35% sulfuric acid (wt/vol), previously cooled to a temperature within the range of from −10° C to 25° C, preferably about 0° C. The temperature during addition and for an additional period of time from 10–60 minutes thereafter, preferably about 30 minutes is maintained within the preferred range. Extraction with a water-immiscible solvent, preferably diethyl ether, washing and drying of the extracts, followed by removal of the solvent gives a residue which is purified by chromatography on silica gel to yield the corresponding aldehyde, a lower alkyl ester of 2-(ω-carboxy-y)cyclopentan-1-on-3-al (IV, R = lower alkyl).

In the foregoing procedure it is also possible to treat the lower alkyl ester of 2-(ω-carboxy-Y)-3-nitromethyl-cyclopentan-1-one with an alkali metal hydroxide to obtain the free acid of formula II in which R is hydrogen, from which the corresponding free acid 2-(ω-carboxy-Y)cyclopentan-1-on-3-al (IV, R = H) is obtained in the manner described above. Alternatively, said last-named compound may also be obtained by treating a lower alkyl ester of 2-(ω-carboxy-Y)-3-nitromethyl-cyclopentan-1-one (II, R = lower alkyl) with an alkali metal hydroxide instead of an alkali metal alkoxide to generate the solution of an alkali metal salt of the corresponding nitronic acid, which is then treated with acid as described above to yield the corresponding free acid of the aldehyde of formula IV in which R is hydrogen. The above aldehyde and its lower alkyl esters are both useful as starting materials in the subsequent step of the process of this invention. However, it is preferred to use one of the lower alkyl esters of the aldehyde of formula IV, preferably the methyl ester, because the subsequent reaction products are more easily purified in the form of their esters than as the corresponding acids.

A solution of a Wittig reagent of the formula (AlkO)$_2$P(O)CH$_2$CO(CH$_2$)$_n$CH$_3$ in which $n$ is an integer of from 1–6 and Alk is an alkyl containing from 1–3 carbon atoms, preferably a dimethyl 2-oxoalkylphosphonate in approximately 5–10 parts, preferably about 7 parts of an aprotic solvent, preferably dimethoxyethane, is added slowly under a blanket of nitrogen to a stirred suspension of approximately one equivalent of an alkali metal hydride, preferably sodium hydride, in approximately 150 parts of an aprotic solvent, preferably dimethoxyethane, and stirring is continued at room temperature for periods of time of from 10–60 minutes, preferably for about 30 minutes. To the resulting solution of the corresponding ylid there is slowly added a solution of approximately three quarters to one equivalent, preferably about 0.85 equivalent of a lower alkyl ester of 2-(ω-carboxy-Y)-cyclopentan-1-on-3-al in about 5 – 10 parts, preferably about 8 parts of an aprotic solvent, preferably dimethoxyethane. The addition is carried out at room temperature over a period of time of from 5–30 minutes, preferably about 10 minutes, and stirring is continued for another 10–60 minutes, preferably for about 30 minutes. Acidification with an aqueous acid, preferably hydrochloric acid, followed by extraction with a water-immiscible solvent, preferably diethyl ether, washing and drying of the extracts, evaporation of the solvent, and chromatography of the residue on silica gel yields the corresponding lower alkyl ester of a 2-(ω-carboxy-Y)-3-(3-oxoalk-1-enyl)cyclopentan-1-one of formula VIII in which R is lower alkyl and $n$ is an integer of from 1 – 6.

Said last-named compound is heated for 1 – 5 hours, preferably for about 2.5 hours, in benzene solution at the reflux temperature of the mixture with ethylene glycol in the presence of a catalytic amount of p-toluenesulfonic acid, to yield the corresponding ethylene ketal, a lower alkyl ester of a 2-($\omega$-carboxy-Y)-3-(3-oxoalk-1-enyl)-cyclopentan-1-one ethylene ketal of formula IX in which R is lower alkyl and $n$ is as defined above. This selective ketalization of the ketone group in position 1 requires critical conditions with respect to the amounts of p-toluenesulfonic acid and ethylene glycol used if the formation of undesirable by-products is to be avoided. When approximately one equivalent of ethylene glycol is used and the amount of p-toluenesulfonic acid does not exceed approximately 10% of the weight of ethylene glycol employed, the above ethylene ketal is the main product and the amounts of undesirable by-products are minimal.

The crude ethylene ketal obtained as described above, without further purification, is dissolved in about 10 parts of a lower alkanol, preferably methanol, and an alkali metal borohydride is added in small portions with constant stirring which is continued for another 20–60 minutes, preferably about 30 minutes, after completion of addition. Evaporation of the lower alkanol, extraction with a water-immiscible solvent, preferably diethyl ether, evaporation of the latter, and chromatography of the residue in silica gel yields the corresponding lower alkyl ester of a 2-($\omega$-carboxy-Y)-3-(3-hydroxyalkyl-1-enyl)-cyclopentan-1-one ethylene ketal of formula X in which R is lower alkyl and n is as defined above. Treatment of said last-named compound with an aqueous acid, preferably p-toluenesulfonic acid in a mixture of a lower alkanol, preferably methanol, and water, and allowing the mixture to stand for 12–24 hours at room temperature yields the corresponding lower alkyl ester of a 2-(o-carboxy-Y)-3-(3-hydroxyalkyl-1-enyl)-cyclopentan-1-one of formula XI in which R is lower alkyl and n is as defined above.

A related aspect of the above process as noted above is the alternative use of the compounds of general formula VIII to yield the diol compounds of formula VIIIa by reduction with an alkali metal borohydride.

When the starting material use in the above process is the methyl ester of 2-(6-carboxyhexyl)cyclopentan-1-on-3-al and the Wittig reagent employed is dimethyl 2-oxoheptylphosphonate of the formula (MeO)$_2$-P(O)CH$_2$CO(CH$_2$)$_n$CH$_3$ in which $n$ = 4, the compound of formula VIII in which Y is CH$_2$—(a)—(CH$_2$)$_m$ wherein (a) is CH$_2$CH$_2$ and $m$ = 3, R is methyl and $n$ = 4 obtained is the methyl ester of 2-(6-carboxyhexyl)-3-(3-oxooct-1-enyl)-cyclopentan1-one also called 9,15-dioxoprost-13-enoic acid methyl ester; the compound of formula IX in which Y is as defined in the last instance, R is methyl and $n$ = 4 obtained from the above compound of formula VIII is 9-ethylenedioxy-15-oxoprost-13-enoic acid methyl ester; the compound of formula X in which Y is as defined in the last instance, R is methyl and $n$ = 4 obtained therefrom is 9-ethylenedioxy-15-hydroxyprost-13-enoic acid methyl ester; and the compound of formula XI in which Y is as defined in the last instance, R is methyl and $n$ = 4 is 15-hydroxy-9-oxoprost-13-enoic acid methyl ester, identical with the same compound described in British Pat. No. 1,218,998, cited above.

The compounds of formula VIII in which R is lower alkyl and $n$ is an integer of from 1 – 6 obtained as described above may be reduced by treatment with hydrogen and a noble metal catalyst, preferably palladium on charcoal, to the corresponding saturated analogs, the lower alkyl esters of a 2-$\omega$-carboxyY)-3 -(3-oxoalk-1yl)-cyclopentan-1one in which Y is (CH$_2$—(a)—(CH$_2$)$_m$ wherein (a) is CH$_2$CH$_2$ and $m$ is an integer from 2 to 4. The saturated analogs of the compounds of formula IX obtained from said last-named compound in the same manner as described above are the corresponding lower alkyl esters of a 2-($\omega$-carboxy-Y)-3-(3-oxoalk-1yl)-cyclopentan-1-one ethylene ketal, from which the corresponding saturated analogs of the compounds of formula X, the corresponding lower alkyl esters of a 2-($\omega$-carboxy-Y)-3(3-hydroxyalk-1-yl)-cuyclopentan-1-one ethylene ketal in which Y is CH$_2$—(a)—(CH$_2$)$_m$ wherein (a) is CH$_2$CH$_2$ and m is an integer from 2 to 4, are obtained by treatment with an alkali metal borohydride in the manner described above. Said last-named compounds yield, upon treatment with an aqueous acid as described above, the saturated analogs of the compounds of formula XI, viz. the corresponding lower alkyl esters of a 2-($\omega$carboxy-Y)-3-(3-hydroxyalk-1yl)-cyclopen-1-one in which Y is (CH$_2$—(a)—(CH$_2$)$_m$ wherein (a) is CH$_2$CH$_2$ and m is an integer from 2 to 4. It is obvious that the above reduction may be carried out with any of the compounds of formulae VIII, IX, X or XI, and that the saturated analogs thus obtained may be used as starting materials in any of the reactions described above. Thus, the compound of formula VIII in which Y is CH$_2$—(a)—(CH$_2$)$_m$ wherin (a) is CH$_2$CH$_2$ and $m$ = 3, R is methyl and $n$, = 4, viz., 9,15-dioxoprost-13-enoic acid methyl ester yields, upon treatment with hydrogen and a noble metal catalyst in the manner described above, 9,15-dioxoprostanoic acid methyl ester, identical with the same compound described in French patent application No. 2,021,234, cited above, and the compound of formula XI in which Y is as described in the last instance, R is methyl and $n$ = 4 yields in the same manner 9-oxo-15-hydroxyprostanoic acid, identical with the same compound described in French patent application No. 2,021,234 cited above.

When it is desired to obtain related compounds containing a hydroxyl rather than a keto function in position 1 of the cyclopentane ring the following variants of the above process may be used.

To a solution of a lower alkyl of 2-($\omega$-carboxy-Y)-3-nitromethyl-cyclopentan-1-one (II, R = lower alkyl) is in a lower alkanol, preferably methanol, approximately one equivalent of sodium borohydride is added in small portions with cooling to about 0° C. After completion of the addition the mixture is stirred for 10–60 minutes, preferably for about 30 minutes, acidified, the lower alkanol evaporated and the residue extracted with a water-immiscible solvent, preferably diethyl ether. Washing, drying, and evaporation of the extracts yields the corresponding lower alkyl ester of 2-($\omega$-carboxy-Y)-3-nitromethyl-cyclopentan-1-ol (III, R = lower alkyl).

Said last-named compound of formula III is treated with an alkali metal lower alkoxide followed by treatment with cold aqueous acid in the same manner as described earlier in this Application for the conversion of the compounds of formula II to those of formula IV, to yield the corresponding lower alkyl ester of 2-($\omega$-carboxy-Y)cyclopentan-1-ol-3al (V, R = lower alkyl, R$^1$ = H).

The same compound may also be obtained by stirring a solution of a lower alkyl ester of 2-(ω-carboxy-Y)-3-nitromethyl-cyclopentan-1-one (II, R = lower alkyl) in a lower alkanol, preferably methanol, with molar excess, preferably about 4–5 equivalents, of an alkali metal hydroxide, preferably sodium hydroxide, for 12–24 hours at room temperature. In this manner the nitro group is converted to the corresponding nitronic acid and the ester group is hydrolyzed in the corresponding free acid, and both groups form the corresponding alkali metal salt. The resulting solution is poured into cold (−10°C to 25° C, preferably in the vicinity of 0° C) aqueous acid, preferably about 4–5 equivalents of sulfuric acid, stirred for 20–120 minutes, preferably for about 60 minutes, and extracted with a water-immiscible solvent, preferably diethyl ether. The extracts are washed, dried, and evaporated, to yield a residue containing the free aldehyde, 2-(ω-carboxy-Y)-cyclopentan-1-on-3-al. The residue is heated in solution in about 6 parts of a lower alkanol, preferably methanol at the boiling point of the mixture of an acid catalyst as exemplified above, preferably p-toluenesulfonic acid in amounts of from about 15% by weight of the above residue, for 1 – 3 hours, preferably for 1.5–2.0 hours. In this manner the corresponding di-(lower alkyl) acetal is formed and the free acid group is re-esterified. The solvent is evaporated from the reaction mixture, the residue extracted with a water-immiscible solvent, preferably diethyl ether, the extracts washed, dried and evaporated, and the residue chromatographed on silica gel, to yield the corresponding lower alkyl ester of 2-(ω-carbamoyl-Y)cyclopentan-1-on-3-al di-(lower alkyl) acetal (VI, R = lower alkyl). When methanol is used as the lower alkanol in the above reaction, the methyl ester of 2-(ω-carboxy-Y)cyclopentan-1-on-3-al dimethyl acetal is obtained (VI, R = Me).

A lower alkyl ester of a 2-(ω-carboxy-Y)-cyclopentan-1-on-3-al di-(lower alkyl) acetal is dissolved in about 10 parts of a lower alkanol, preferably methanol, and an alkali metal borohydride, preferably sodium borohydride, is added with cooling. The mixture is stirred for 5–60 minutes, preferably for about 10 minutes, diluted with a water-immiscible solvent, preferably diethyl ether, and with saturated ammonium chloride, the organic phase separated, washed with saturated sodium chloride solution, dried, and evaporated to give a residue containing the corresponding lower alkyl ester of 2-(ω-carboxy-Y)cyclopentan-1-ol-3-al di-(lower alkyl) acetal (VII, R = lower alkyl). Said last-named residue is stirred at room temperature with a solution of an acid in a water-miscible ether-type solvent, preferably about 25% sulfuric acid in tetrahydrofuran, the mixture extracted with a water-immiscible solvent, preferably diethyl ether, the extracts washed with water, dried, and evaporated, to give a residue containing the corresponding lower alkyl ester of 2-(ω-carboxy-Y)cyclopentan-1-ol-3-al (V, R = lower alkyl, R$^1$ = H), identical with the same compound obtained as described above.

This last-named residue is dissolved in a halogenated hydrocarbon solvent, preferably methylene chloride, dihydropyran and an acid catalyst as exemplified above, preferably p-toluenesulfonic acid is washed, the mixture is stirred at room temperature for 30–120 minutes, preferably for about 60 minutes, diluted with a halogenated hydrocarbon solvent, preferably methylene chloride, washed with water, dried, and evaporated to give a residue which is purified by chromatography on silica gel. The corresponding lower alkyl ester of 2-(ω-carboxy-Y)-1-tetrahydropyran-2-yloxy-cyclopentan-3-al (V, R = lower alkyl, R$^1$ = tetrahydrofuran-2-yl) is obtained in this manner.

In a related variant of the above procedure the free acids of 2-(ω-carboxy-Y)-3-nitromethylcyclopentan-1-one (II, R = H), 2-(ω-carboxy-Y)-3-nitromethylcyclopentan-1-ol (III, R = H) and 2-(ω-carboxy-Y)cyclopentan-1-ol-3-al (V, R = R$^1$ = H), or preferably the corresponding lower alkyl esters thereof, in which Y is CH$_2$—(a)—(CH)$_m$ wherein (a) is CH=CH and m is an integer from 2 to 4, may be treated with hydrogen in the presence of a noble metal catalyst, preferably palladium on charcoal, to yield their corresponding derivatives of formulae II, III and V, respectively, in which Y is CH$_2$—(a)—(CH$_2$)$_m$ wherein (a) is CH$_2$CH$_2$ and m is an integer from 2 to 4.

The ylid of a Wittig reagent of the formula (AlkO)$_2$P(O)CH$_2$CO(CH$_2$)$_n$CH$_3$ in which n is an integer of from 1 – 6 and Alk is an alkyl containing from 1 –3 carbon atoms, preferably a dimethyl 2-oxoalkylphosphonate, is prepared in the same manner as described earlier in this Application. A solution of a lower alkyl ester of 2-(ω-carboxy-Y)cyclopentan-1-ol-3-al tetrahydropyranyl ether (V, R = lower alkyl, R$^1$ = tetrahydropyranyl) in an aprotic solvent, preferably dimethoxyethane, is added slowly as described earlier and the mixture is heated to 25°–80° C, preferably to about 60°–65° C, for 10–60 minutes, preferably for about 30 minutes, cooled, and acidified with an aqueous solution of a weak acid, preferably about 50% aqueous acetic acid. Extraction with a water-immiscible solvent, preferably diethyl ether, washing of the extracts, drying, and evaporation followed by chromatography of the residue on silica gel yields the corresponding lower alkyl ester of a 2-(ω-carboxy-Y)-3-(3-oxoalk-1-enyl)cyclopentan-1-ol tetrahydropyran-2-yl ether (XII, R = lower alkyl, R$^1$ = 2-tetrahydropyranyl, n = 1 – 6).

The further conversion of the above compounds of formula XII to the corresponding compounds of formula XI is carried out in the same manner as described in British Pat. No. 1,218,998 cited above. Treatment of a compound of formula XII with an alkali metal borohydride yields the corresponding lower alkyl ester of a 2-(ω-carboxy-Y)-3-(3-hydroxyalk-1-enyl)-cyclopentan-1-ol tetrahydropyran-2-yl ether. Acylation of said last-named compound with a lower alkanoic acid anhydride in the presence of a base, preferably pyridine, gives the corresponding lower alkyl ester of a 2-(ω-carboxy-Y)-3-(3-(lower acyloxy)alk-1-enyl)-cyclopentan-1-ol tetrahydropyranyl ether. Treatment of said last-named compound with acid removes the protective ether group and gives the corresponding lower alkyl ester of a 2-(ω-carboxy-Y)-3-(3-(lower acyloxy)alk-1-enyl)-cyclopentan-1-ol. Said last-named compound is treated with an agent capable of converting a hydroxy function to the corresponding keto function, preferably with chromic acid in acetone, to give the corresponding lower alkyl ester of a 2-(ω-carboxy-Y)-3-(3-(lower acyloxy)alk-1-enyl)cyclopentan-1one. And treatment of said last-named compound in the manner described in British Patent 1,218,998 with an alkali metal hydroxide or carbonate gives the corresponding compound of formula XI, a 2-(ω-carboxy-Y)-3-(3-hydroxyalk-1-enyl)cyclopentan-1-one either in the form of its free acid or of its lower alkyl ester (XI, R = H or lower alkyl, n = 1–6)

When the Wittig reagent used in the reaction described above is (MeO)$_2$P(O)CH$_2$CO(CH$_2$)$_4$CH$_3$, i.e. dimethyl 2-oxoheptylphosphonate, and the compound of formula V used is the methyl ester of 2-(6-carboxyhexyl)cyclopentan-1-ol-3-al tetrahydropyranyl ether, the compound of formula XII obtained is the methyl ester of 2-(6-carboxyhexyl)-3-(3-oxooct-1-enyl)-cyclopentan-1-ol tetrahydropyranyl ether, also called the tetrahydropyranyl ether of 9-hydroxy-15-oxoprost-13-enoic acid methyl ester (XII; Y = $(CH_2)_6$, R = Me, $R^1$ = tetrahydropyran-2-yl, n = 4), identical with the same compound described in British Pat. No. 1,218,998 cited above.

Carrying out the sequence of reactions described in British Pat. No. 1,218,998 cited above with said last-named compound, there are obtained the corresponding tetrahydropyranyl ether of 9,15-dihydroxyprost-13-enoic acid methyl ester, from which the corresponding tetrahydropyranyl ether of 15-acetoxy-9-hydroxyprost-13-enoic acid methyl ester is obtained by treatment with acetic anhydride in pyridine. Said last-named compound is treated with acid to give 15-acetoxy-9-hydroxyprost-13-enoic acid methyl ester, which is treated with chromic acid in acetone to yield 15-acetoxy-9-oxoprost-13-enoic acid methyl ester. Treatment of said last-named compound with sodium hydroxide or sodium carbonate gives 15-hydroxy-9-oxoprost-13-enoic acid (XI; Y = $(CH_2)_6$, R = H, n = 4) and the methyl ester (XI; Y = $(CH_2)_6$, R = Me, n = 4), respectively, both last-named compounds being identical with the same compound described in British Pat. No. 1,218,998 cited above.

When the Wittig reagent used in the reaction described above is $(MeO)_2P(O)CH_2CO(CH_2)_4CH_3$, i.e. dimethyl 2-oxo heptylphosphonate, and the compound of formula V used is the methyl ester of 2-(6-carboxyhex-2-enyl)cyclopentan-1-ol-3-al tetrahydropyranyl ether, the compound of formula XII obtained is the methyl ester of 2-(6-carboxyhex-2-enyl)-3-(3-oxooct-1-enyl)cyclopentan-1-ol tetrahydropyranyl ether, also called the tetrahydropyranyl ether of 9-hydroxy-15-oxo-prosta-5,13-dienoic acid methyl ester (XII; Y = $CH_2CH=CH(CH_2)_3$, R = Me, $R^1$ = tetrahydropyranyl, n = 4).

Again carrying out the sequence of reactions described in British Pat. No. 1,218,998, cited above, with said last-named compound, there are obtained the corresponding tetrahydropyranyl ether of 9,15-dihydroxyprosta-5,13-dienoic acid methyl ester, from which the corresponding tetrahydropyranyl ether of 15-acetoxy-9-hydroxyprosta-5,13-dienoic acid methyl ester is obtained by treatment with acetic anhydride in pyridine. Said last-named compound is treated with acid to give 15-acetoxy-9-hydroxyprosta-5,13-dienoic acid methyl ester, which is treated with chromic acid in acetone to yield 15-acetoxy-9-oxoprosta-5,13-dienoic acid methyl ester. Treatment of said last-named compound with sodium hydroxide or sodium carbonate, gives 15-hydroxy-9-oxoprosta-5,13-dienoic acid (XI; Y = $CH_2CH=CH(CH_2)_3$, R = H, n = 4) and the methyl ester (XI; Y = $CH_2CH=CH(CH_2)_3$, R = Me, n = 4), respectively.

The compounds of the general formula XI may be transformed further into useful derivatives thereof. Thus, treatment of a compound of formula XI with hydrogen in the presence of a noble metal catalyst, preferably palladium on charcoal, yields the corresponding lower alkyl ester of 2-(ω-carboxy-Y)-3-(3-hydroxyalk-1-yl) cyclopentan-1-one (XIII; Y = $CH_2$—(a)—$(CH_2)_m$ wherein (a) is $CH_2CH_2$ $CH=CH$ or $C\equiv CH$ and m = 2 – 4, R = lower alkyl, n = 1 – 6).

When the starting material of the formula XI in which Y = $(CH_2)_6$ and m = 4, either as the free acid (R = H) or as the methyl ester (R = Me) is treated in the above manner, 9-oxo-15-hydroxyprostanoic acid (XIII; Y = $(CH_2)_6$, R = H, n = 4) or its methyl ester (XIII; Y = $(CH_2)_6$, R = Me, n = 4) are respectively obtained, both identical with the same compounds described in French patent application No. 2,021,234 cited above. Said compounds of formula XIII may be treated with an alkali metal borohydride, preferably sodium borohyride, to yield the corresponding lower alkyl esters of 2-(ω-carboxy-Y)-3-(3-hydroxyalk-1-yl)-cyclopentan-1α-ol (XIV; Y is $CH_2$—(a)—$(CH_2)_m$ wherein (a) is $CH_2CH_2$ and m = 2 – 4, R = lower alkyl, $R^2$ = H, $R^3$ = OH, n = 1 – 6) or of 2-(ω-carboxy-Y)-3-(3-hydroxyalk-1-yl)cyclopentan-1β-ol (XIV; Y is as defined in the last instance, R = lower alkyl, $R^2$ = OH, $R^3$ = H, n = 1 – 6). In this case, when the starting material of formula XIII is 9-oxo-15-hydroxyprostanoic acid or its methyl ester there are obtained 9α,15ζ-dihydroxyprostanoic acid or its ethyl ester (XIV; Y = $(CH_2)_6$, R = H or Me, $R^2$ = H, $R^3$ = OH, n = 4) and 9β,15ζ-dihydroxyprostanoic acid or its methyl ester, (XIV; Y = $(CH_2)_6$, R = H or Me, $R^2$ = OH, $R^3$ = H, n = 4), respectively, both identical with the same compounds described in French patent application No. 2,021,234, cited above.

In addition, as indicated before, the compounds of general formula XI may be transformed also into diol compounds of general formula VIIIa by reduction with an alkali metal borohydride.

The starting materials of formula I of this invention are either known, for example, 2-(6-carboxyhexyl)-cyclopent-2-en-1-one, described by Bagli and Bogri in U.S. Pat. No. 3,432,541, issued Mar. 11, 1969, or they may be prepared by the following convenient process which is represented schematically in the following manner:

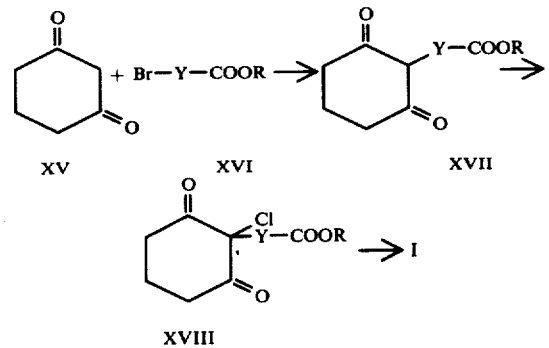

in which Y and R are as defined in the first instance.

With reference to the first step of this process 1,3-cyclohexadione (XV) is condensed with an appropriate ω-bromoacid or preferably an appropriate lower alkyl ω-bromoester of formula XVI in the presence of an alkali metal alkoxide in a lower alkanol, preferably sodium methoxide in methanol, to give the dioneester of formula XVII.

The ω-bromoacids and the lower alkyl ω-bromoesters of formula XVI are either known or may be prepared by known methods; for example, see "Rodd's Chemistry of the Carbon Compounds", S. Coffey, Ed., Vol. 1c, 2nd Ed., pp. 201 – 215. In this respect a convenient method for preparing the lower alkyl ω-bromoesters of formula XVI in which Y is $CH_2$—(a)—$(CH_2)_m$ wherein (a) is C≡C and m is an integer from 2 to 4 involves condensing propargyl alcohol tetrahydropyran-2-yl ether, described by R. G. Jones and M. J. Mann, J. Amer. Chem. Soc., 75, 4048 (1953), with a dihaloalkane of formula $Br(CH_2)_mCl$ in which m is an integer from 2 to 4 according to the procedure used by A. I. Rachlin, et al., J. Org. Chem., 26, 2688 (1961), to prepare 1-[(tetrahydropyran-2-yl)oxy]-6-chloro-2-hexyne. The resulting ω-tetrahydropyranyloxyalkynyl chloride is hydrolyzed, for example, with p-toluenesulfonic acid is aqueous methanol, to its corresponding alcohol of formula $HOCH_2C≡C(CH_2)_mCl$ (m = 2 - 4). The latter compound is then treated with potassium or sodium cyanide in a lower alkanol, preferably with potassium cyanide in ethanol, at reflux temperature for eight to 24 hours to give the cyanide of formula $HOCH_2C≡CH(CH)_mCN$ (m = 2 - 4). Subsequently a solution containing an excess of potassium hydroxide in water is added to the reaction mixture of the cyanide and the resultant mixture is heated at reflux for a further ten to 20 hours whereby the cyanide is converted to the corresponding hydroxyacid. The latter compound is then brominated by treatment with phosphorus tribromide in ether solution in the presence of a suitable proton acceptor, for example, pyridine, to yield the corresponding bromoacid, which is esterified with a lower alkanol, for example, methanol in the presence of a suitable acid catalyst, for example, p-toluenesulfonic acid, to give the desired lower alkyl bromoester of formula XVI. If desired the latter compounds are hydrogenated in the presence of Lindlar catalyst or a noble metal catalyst, for example, palladium on charcoal, to give the corresponding lower alkyl bromoesters of formula XVI in which Y is $CH_2$—(a)—$(CH_2)_m$ wherein (a) is CH≡CH or $CH_2Ch_2$, respectively, and m an integer from 2 to 4.

With reference to the second step of the above process, the dioneester of formula XVII is treated with t-butyl hypochlorite in the manner described by G. Buchi and B. Egger, J. Org. Chem., 36, 2021 (1971), to yield the chloro derivative XVIII. The latter treatment is performed preferably under a nitrogen atmosphere using dry chloroform as a solvent. Thereafter, the chloro derivative is treated in a hydrocarbon solvent in the presence of an alkali metal carbonate at temperatures from 100° to 150° C. from about 5 to 25 hours whereby ring contraction is effected to yield the desired starting material of formula I. Preferred conditions for the treatment of the chloro derivative include subjecting solution of the compound in xylene to reflux for 16 hours in the presence of anhydrous sodium carbonate, followed by water washing, drying and evaporation of the xylene phase to give the starting material of formula I.

If desired the latter compounds in which Y is $CH_2$—(a)—$(CH_2)_m$ wherein (a) is C≡C and m is an integer from 2 to 4 may be subjected to hydrogenation in the presence of Lindar catalyst to give the corresponding starting materials of formula I in which Y is $CH_2$—(a)—$(Ch_2)_m$ wherein (a) is CH≡CH and m is an integer from 2 to 4.

The following formulae and examples illustrate further this invention.

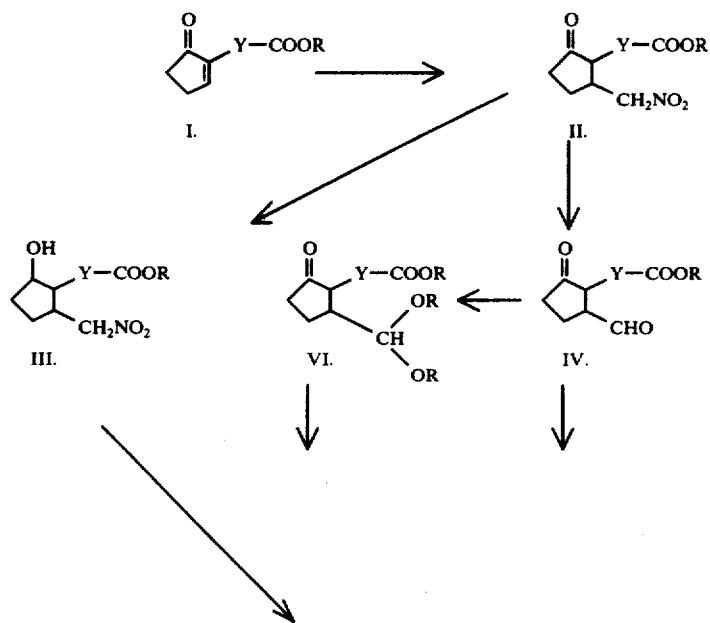

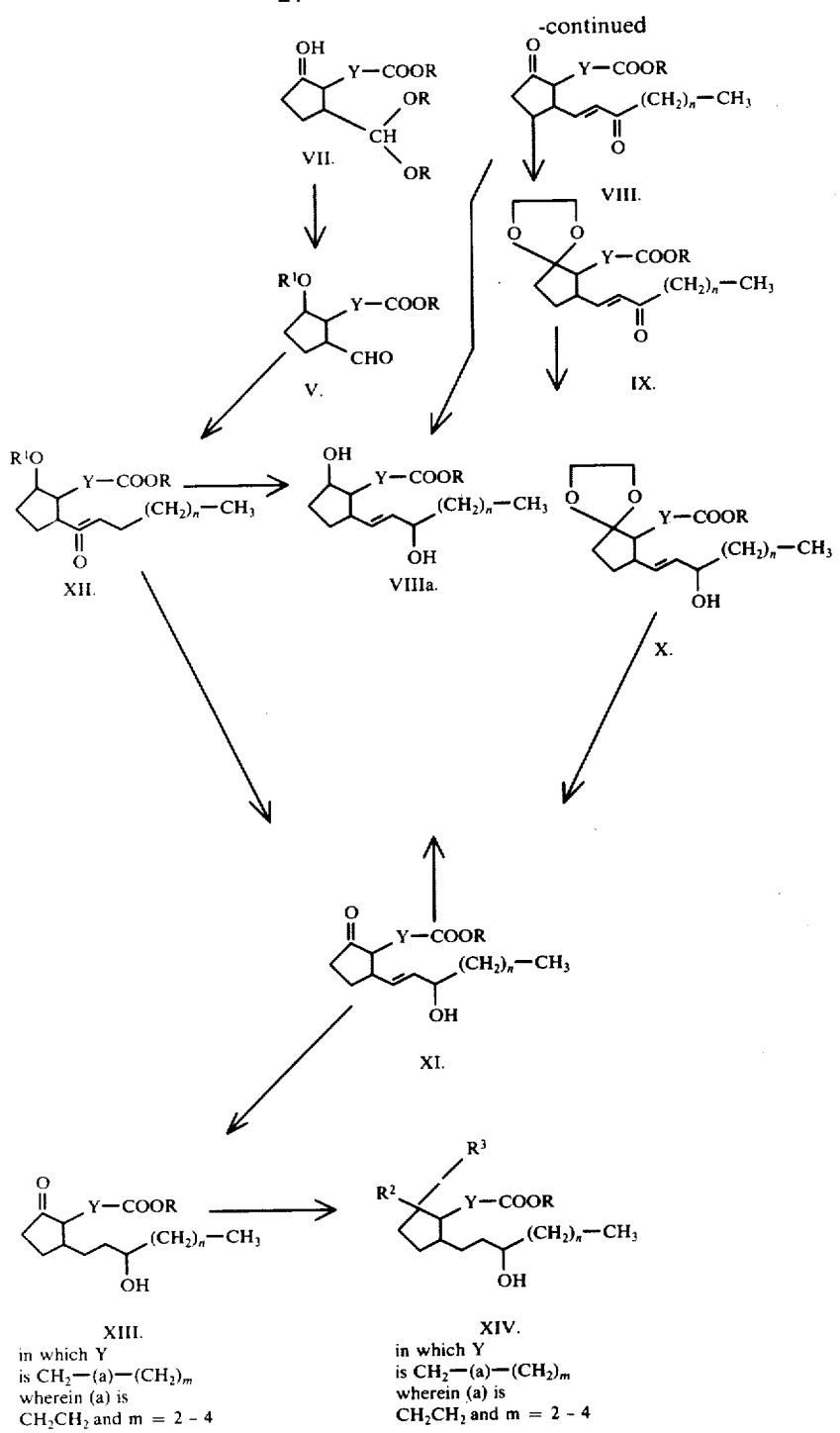

EXAMPLE 1

To a solution of nitromethane (76 g) in dry methanol (70 ml) there are added at 60° C., simultaneously, a solution of sodium methoxide prepared from sodium (14 g) in methanol (346 ml) and a solution of 2-(6-carboxyhexyl)-cyclopent-2-en-1-one methyl ester (111 g) in methanol (150 ml). The reaction mixture is left at 60° - 65° (bath temperature) for 2 hours, cooled, and 50% acetic acid (108 ml) is added. The solvent is removed under reduced pressure. The residue is taken in ether, washed carefully with 5% sodium carbonate three times, then with water, dried and the solvent is removed to yield a residue. This is chromatographed on a silica gel column (1.5 kg) in 20% acetonehexane, and the first 22 fractions yield 2-(6-carboxyhexyl)-3-nitromethyl-cyclopentan-1-one methyl ester, $\gamma_{max}^{Film}$ 1727, 1550 cm$^1$, NMR: (CDCl$_3$) 3.59, 4.5δ, also identified by elemental analysis.

In the same manner, when using the ethyl, propyl, isopropyl, n-butyl, n-pentyl, or n-hexyl esters of 2-(6-carboxyhexyl)-cyclopent-2-en-1-one as starting material and proceeding as above using the appropriate alkoxide in the appropriate alkanol, the ethyl, propyl, isopropyl, n-butyl, n-pentyl, and n-hexyl esters of 2-(6-carboxyhexyl)-3-nitromethyl-cyclopentan-1-one are respectively obtained.

Likewise, when using the methyl, ethyl, propyl, isopropyl, n-butyl, n-pentyl or n-hexyl esters of 2-(5-carboxypentyl)cyclopent-2-en-1-one or 2-(7-carboxyheptyl)cyclopent-2-en-1-one as starting material, the methyl, ethyl, propyl, isopropyl, n-butyl, n-pentyl and n-hexyl esters of 2-(5-carboxypentyl)-3-nitromethyl-cyclopentan-1-one and 2-(7-carboxyheptyl)-3-nitromethyl-cyclopentan-1-one are respectively obtained.

Likewise, when using the methyl, ethyl, propyl, isopropyl, n-butyl, n-pentyl or n-hexyl esters of 2-(5-carboxypent-2-enyl)cyclopent-2-en-1-one, 2-(6-carboxyhex-2-enyl)cyclopent-2-en-1-one, 2-(7-carboxyhept-2-enyl)-cyclopent-2-en-1-one, 2-(5-carboxypent-2-ynyl)-cylopent-2-en-1-one, 2-(6-carboxyhex-2-ynyl)cyclopent-2-en-1-one, or 2-(7-carboxyhept-2-ynyl)cyclopent-2-en-1-one, as starting materials, the methyl, ethyl, propyl, isopropyl, n-butyl, n-pentyl and n-hexyl esters of 2-(5-carboxypent-2-enyl)-3-nitromethyl-cyclopentan-1-one, 2-(6-carboxyhex-2-enyl)-3-nitromethyl-cyclopentan-1-one, 2-(7-carboxyhept-2-enyl)-3-nitromethyl-cyclopentan-1-one, 2-(5-carboxypent-2-ynyl)-3-nitromethyl-cyclopentan-1-one, 2-(6-carboxyhex-2-ynyl)-3-nitromethyl-cyclopentan-1-one, and 2-(7-carboxyhept-2-ynyl)-3-nitromethyl-cyclopentan-1-one, are respectively obtained.

2-(6-Carboxyhex-2-enyl)-3-nitromethyl-cyclopentan-1-one has $\gamma_{max}^{Film}$ 1735, 1550 cm$^{-1}$.

2-(6-Carboxyhex-2-ynyl)-3-nitromethyl-cyclopentan-1-one has $\gamma_{max}^{Film}$ 1730, 1550 cm$^{-1}$.

EXAMPLE 2

2-(6-Carboxyhexyl)-3-nitromethyl-cyclopentan-1-one methyl ester (12 g) is added to a solution of sodium methoxide (1.8 g of sodium in 120 ml methanol) and the mixture is allowed to stand at room temperature for 30 minutes. The above solution is added with stirring to cold (0° C) aqueous sulfuric acid (111 ml H$_2$SO$_4$ in 708 ml water) over a period of 45 minutes, stirred at 0° C for an additional 30 minutes and extracted with ether. The ether extract is washed to neutrality with saturated sodium chloride solution, dried over magnesium sulfate and evaporated under reduced pressure to yield a residue which is chromatographed on silica gel (600 g) and eluted with 7% methanol in benzene to give 2-(6-carboxyhexyl)cyclopentan-1-on-3-al methyl ester, $\gamma_{max}^{Film}$ 2700 cm$^{-1}$.

In the same manner, when using the ethyl, propyl, isopropyl, n-butyl, n-pentyl, and n-hexyl esters of 2-(6-carboxyhexyl)-3-nitromethyl-cyclopentan-1-one as starting material and proceeding as above, the ethyl, propyl, isopropyl, n-butyl, n-pentyl, and n-hexyl esters of 2-(6-carboxyhexyl)cyclopentan-1-on-3-al are respectively obtained.

Likewise, when using the methyl, ethyl, propyl, isopropyl, n-butyl, n-pentyl or n-hexyl esters of
2-(5-carboxypentyl)-3-nitromethyl-cyclopentan-1-one or
2-(7-carboxyheptyl)-3-nitromethyl-cyclopentan-1-one as starting material, the methyl, ethyl, propyl, isopropyl, n-butyl, n-pentyl and n-hexyl esters of
2-(5-carboxypentyl)cyclopentan-1-on-3-al and
2-(7-carboxyheptyl)cyclopentan-1-on-3-al are respectively obtained.

Likewise, when using the methyl, ethyl, propyl, isopropyl, n-butyl, n-pentyl or n-hexyl esters of
2-(5-carboxypent-2-enyl)-3-nitromethyl-cyclopentan-1-one,
2-(6-carboxyhex-2-enyl)-3-nitromethyl-cyclopentan-1-one,
2-(7-carboxyhept-2-enyl)-3-nitromethyl-cyclopentan-1-one, 2-(5-carboxypent-2-ynyl)-3-nitromethyl-cyclopentan-1-one,
2-(6-carboxyhex-2-ynyl)-3-nitromethyl-cyclopentan-1-one, or
2-(5-carboxyhept-2-ynyl)-3-nitromethyl-cyclopentan-1-one, as starting materials, the methyl, ethyl, propyl, isopropyl, n-butyl, n-pentyl and n-hexyl esters of
2-(5-carboxypent-2-enyl)cyclopentan-1-on-3-al,
2-(6-carboxyhex-2-enyl)cyclopentan-1-on-3-al,
2-(7-carboxyhept-2-enyl)cyclopentan-1-on-3-al,
2-(5-carboxypent-2-ynyl)cyclopentan-1-on-3-al,
2-(6-carboxyhex-2-ynyl)cyclopentan-1-on-3-al, and
2-(7-carboxyhept-2-ynyl)cyclopentan-1-on-3-al, are respectively obtained.

EXAMPLE 3

Sodium hydride (57%, 1.27 g) is washed by decantation several times with low boiling petroleum ether in an atmosphere of nitrogen and the solvent is removed under reduced pressure. The dried sodium hydride is suspended in 1,2-dimethoxyethane (200 ml) and a solution of dimethyl 2-oxoheptylphosphonate (6.7 g) in 1,2-dimethoxyethane (50 ml) is added with stirring over a period of 10 minutes at low temperature. Stirring is continued for 30 minutes and the methyl ester of 2-(6-carboxyhexyl)cyclopentan-1-on-3-al (6.4 g) in 1,2-dimethoxyethane (50 ml) is added over a period of 10 minutes with stirring which is continued for another 30 minutes. The mixture is acidified with aqueous hydrochloric acid (30 ml) and extracted with ether. The ether extracts are washed to neutrality, dried over magnesium sulfate and evaporated under reduced pressure to give a residue which is chromatographed on silica gel and eluted with 40% ether in hexane to yield 9,15-dioxoprost-13-enoic acid methyl ester, $\gamma_{max}^{Film}$ 1690, 1670, 1630, 1370 cm$^{-1}$; NMR: (CDCl$_3$) 6.76, 6.10, $\delta$3.63.

In the same manner, by using as starting materials the ethyl, propyl, isopropyl, n-butyl, n-pentyl or n-hexyl esters of 2-(6-carboxyhexyl)cyclopentan-1-on-3-al there are obtained the ethyl, propyl, isopropyl, n-butyl, n-pentyl, and n-hexyl esters of 9,15-dioxoprost-13-enoic acid.

Again in the same manner, but using as starting materials the dimethyl 2-oxobutyl-, 2-oxopentyl-, 2-oxohexyl-, 2-oxooctyl-, or 2-oxononyl-phosphonates and reacting them with the methyl, ethyl, propyl, isopropyl, n-butyl, n-pentyl, or n-hexyl esters of 2-(6-carboxyhexyl)cyclopentan-1-on-3-al, there are obtained the methyl, ethyl, propyl, isopropyl, n-butyl, n-pentyl, and n-hexyl esters of
2-(6-carboxyhexyl)-3-(3-oxopent-1-enyl)-cyclopentan-1-one,
2-(6-carboxyhexyl)-3-(3-oxohex-1-enyl)-cyclopentan-1-one,
2-(6-carboxyhexyl)-3-(3-oxohept-1-enyl)-cyclopentan-1-one,
2-(6-carboxyhexyl)-3-(3-oxonon-1-enyl)-cyclopentan-1-one, and
2-(6-carboxyhexyl)-3-(3-oxodec-1-enyl)-cyclopentan-1-one, respectively.

Again in the same manner, but using as starting materials the Wittig reagents, dimethyl 2-oxobutyl-, 2-oxopentyl-, 2-oxohexyl-, 2-oxoheptyl-, 2-oxooctyl-, or 2-oxononyl-phosphonates and reacting them with the methyl, ethyl, propyl, isopropyl, n-butyl, n-pentyl, or n-hexyl esters of 2-(5-carboxypentyl)cyclopentan-1-on-3-al there are obtained.

2-(5-carboxypentyl)-3-(3oxopent-1-enyl)cyclopentan-1-one, 2-(5-carboxypentyl)-3-(3-oxohex-1-enyl)cyclopentan-1-one, 2-(5-carboxypentyl)-3-(3-oxohept-1-enyl)cyclopentan-1-one, 2-(5-carboxypentyl)-3-(3-oxooct-1-enyl)cyclopentan-1-one, 2-(5-carboxypentyl)-3-(3-oxonon-1-enyl)cyclopentan-1-one, and 2-(5-carboxypentyl)-3-(3-oxodec-1-enyl)cyclopentan-1-one, methyl, ethyl, propyl, isopropyl, n-butyl, n-pentyl, and n-hexyl esters, respectively.

Again in the same manner, but using a starting materials the preceding, respective Wittig reagents and reacting them with the methyl, ethyl, propyl, isopropyl, n-butyl, n-pentyl, or n-hexyl esters of 2-(7-carboxyheptyl)cyclopentan-1-on-3-al there are obtained.

2-(7-carboxyheptyl)-3-(3-oxopent-1-enyl)cyclopentan-1-one, 2-(7-carboxyheptyl)-3-(3-oxohex-1-enyl)cyclopentan-1'-one, 2-(7-carboxyheptyl)-3-(3-oxohept-1-enyl)cyclopentan-1-one, 2-(7-carboxyheptyl)-3-(3-oxooct-1-enyl)cyclopentan-1-one, 2-(7-carboxyheptyl)-3-(3-oxonon-1-enyl)cyclopentan-1-one, and 2-(7-carboxyheptyl)-3-(3-oxodec-1-enyl)cyclopentan-1-one methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl esters of 2-(5-carboxypent-2-enyl)cyclopentan-1-on-3-al there are obtained.

2-(5-carboxypent-2-enyl)-3-(3-oxopent-1-enyl)cyclopentan-1-one, 2-(5-carboxypent-2-enyl)-3-(3-oxohex-1-enyl)cyclopentan-1-one, 2-(5-carboxypent-2-enyl)-3-(3-oxohept-1-enyl)cyclopentan-1-one, 2-(5-carboxypent-2-enyl)-3-(3-oxooct-1-enyl)cyclopentan-1-one, 2-(5-carboxypent-2-enyl)-3-(3-oxonon-1-enyl)cyclopentan-1-one, and 2-(5-carboxypent-2-enyl)-3-(3-oxodec-1-enyl)cyclopentan-1-one methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl esters of 2-(6-carboxyhex-2-enyl)cyclopentan-1-on-3-al there are obtained 2-(6-carboxyhex-2-enyl)-3-(3-oxopent-1-enyl)cyclopentan-1-one, 2-(6-carboxyhex-2-enyl)-3-(3-oxohex-1-enyl)cyclopentan-1-one, 2-(6-carboxyhex-2-enyl)-3-(3-oxohept-1-enyl)cyclopentan-1-one, 2-(6-carboxyhex-2-enyl)-3-(3-oxooct-1-enyl)cyclopentan-1-one, 2-(6-carboxyhex-2-enyl)-3-(3-oxonon-1-enyl)cyclopentan-1-one, and 2-(6-carboxyhex-2-enyl)-3-(3-oxodec-1-enyl)cyclopentan-1-one, methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl ester of 2-(7-carboxyhept-2-enyl)cyclopentan-1-on-3-al there are obtained.

2-(7-carboxyhept-2-enyl)-3-(3-oxopent-1-enyl)cyclopentan-1-one, 2-(7-carboxyhept-2-enyl)-3-(3-oxphex-1-enyl)cyclopentan-1-one, 2-(7-carboxyhept-2-enyl)-3-(3-oxohept-1-enyl)cyclopentan-1-one, 2-(7-carboxyhept-2-enyl)-3-(3-oxooct-1-enyl)cyclopentan-1-one, 2-(7-carboxyhept-2-enyl)-3-(3-oxonon-1-enyl)cyclopentan-1-one, and 2-(7-carboxyhept-2-enyl)-3-(3-oxodec-1-enyl)cyclopentan-1-one methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl esters of 2-(5-carboxypent-2-ynyl)cyclopentan-1-on-3-al there are obtained.

2-(5-carboxypent-2-ynyl)-3-(3-oxopent-1enyl)cyclopentan-1-one, 2-(5-carboxypent-2-ynyl)-3-(3-oxohex-1-enyl)cyclopentan-1-one, 2-(5-carboxypent-2-ynyl)-3-(3-oxohept-1-enyl)cyclopentan-1-one, 2-(5-carboxypent-2-ynyl)-3-(3-oxooct-1-enyl)cyclopentan-1-one, 2-(5-carboxypent-2-ynyl)-3-(3-oxono-1-enyl)cyclopentan-1-one, and 2-(5-carboxypent-2-ynyl)-3-(3-oxodec-1-enyl)cyclopentan-1-one methyl, ethyl, propyl, isopropyl, n-butyl, n-pentyl, and n-hexyl esters, respectively.

Again in the same manner, but using as starting material the preceding respective Wittig reagents and reacting them wiuth the methyl, ethyl, propyl, isopropyl, n-butyl, n-pentyl, or n-hexyl ester of 2-(6-carboxyhex-2-ynyl)cyclopentan-1-on-3-al there are obtained 2-(6-carboxhex-2-ynyl)-3-(3-oxopent-1-enyl)cyclopentan-1-one, 2-(6-carboxyhex-2-ynyl)-3-(3-oxohex-1-enyl)cyclopentan-1-one, 2-(6-carboxyhex-2-ynyl)-3-(3-oxohept-1-enyl)cyclopentan-1-one, 2-(6-carboxyhex-2-ynyl)-3-(3-oxooct-1-enyl)cyclopentan-1-one 2-(6-carboxyhex-2-ynyl)-3-(3-oxonon-1-enyl)cyclopentan-1-one, and 2-(6-carboxyhex-2-ynyl)-3-(3-oxodec-1-enyl)cyclopentan-1-one methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl esters of 2-(7-carboxyhept-2-ynyl)cyclopentan-1-on-3-al there are obtained 2-(7-carboxyhept-2-ynyl)-3-(3-oxopent-1-enyl)cyclopentan-1-one, 2-(7-carboxyhept-2-ynyl)-3-(3-oxohex-1-enyl)cyclopentan-1-one, 2-(7-carboxyhept-2-ynyl)-3-(3-oxohept-1-enyl)cyclopentan-1-one, 2-(7-carboxyhept-2-ynyl)-3-(3-oxooct-1-enyl)cyclopentan-1-one, 2-(7-carboxyhept-2-ynyl)-3-(3-oxonon-1-enyl)cyclopentan-1-one, and 2-(7-carboxyhept-2-ynyl)-3-(3-oxodec-1-enyl)cyclopentan-1-one, methyl, ethyl, propyl, isopropyl, n-butyl, n-pentyl, and n-hexyl esters, respectively.

EXAMPLE 4

A mixture if 9,15-dioxoprost-13-enoic acid methyl ester (2.0 g) benzene (50 ml), p-toluenesulfonic acid (37 mg) and ethylene glycol (372 mg) is refluxed for 2.5 hours, diluted with ether, washed neutral with water, dried over magnesium sulfate, and evaporated under reduced pressure. The residue containing 9-ethylenedioxy-15-oxoprost-13-enoic acid methyl ester is taken up in methanol (20 ml) and treated with sodium borohydride (300 mg) in small portions with stirring which is continued for 30 minutes. The solvent is evaporated under reduced pressure, the residue taken up in ether, washed to neutrality with water, dried over magnesium sulfate, and the solvent evaporated under reduced pressure. The residue is chromatographed on silica gel (140 g) and eluted with 40% ether in hexane to yield 9-ethylenedioxy-15-hydroxyprost-13-enoic acid methyl ester, $\gamma_{max}^{Film}$ 3460, 1740, 1037, 975, 950 cm$^{-1}$.

EXAMPLE 5

A mixture of 9-ethylenedioxy-15-hydroxyprost-13-enoic acid methyl ester (35 mg), methanol (3 ml) water (0.5 ml) and p-toluenesulfonic acid (10 mg) is allowed to stand at room temperature overnight, taken up in ether, washed to neutrality with water, dried over magnesium sulfate and the solvent evaporated under reduced pressure to yield 15-hydroxy-9-oxoprost-13-enoic acid methyl ester $\gamma_{max}^{Film}$ 3450, 1745 cm$^{-1}$, identical to the compound of the same name described in British Pat. No. 1,218,998, cited above.

By following serially the procedures of Examples 4 and 5 but using as a starting material in Example 4, the ethyl, propyl, isopropyl, n-butyl, n-pentyl, n-hexyl esters of 9,15-dioxoprost-13-enoic acid, or one of the remaining methyl, ethyl, propyl, isopropyl, n-butyl, n-pentyl or n-hexyl esters of the homologs of 9,15-dioxoprost-13-enoic acid, as listed in Example 3, instead of 9,15-dioxoprost-13-enoic acid methyl esters, then the ethyl, propyl, isopropyl, n-butyl, n-pentyl, and n-hexyl esters of 15-hydroxy-9-oxoprost-13-enoic acid; the methyl, ethyl, propyl, isopropyl, n-butyl, n-pentyl, and n-hexyl esters of 2-(6-carboxyhexyl)-3-(3-hydroxypent-1-enyl)cyclopentan-1-one, 2-(6-carboxyhexyl)-3-(3-hydroxyhex-1-enyl)cyclopentan-1-one, 2-(6-carboxyhexyl)-3-(3-hydroxyhept-1-enyl)cyclopentan-1-one, 2-(6-carboxyhexyl)-3-(3-hydroxynon-1-enyl)cyclopentan-1-one, and 2-(6-carboxyhexyl)-3-(3-hydroxydec-1-enyl)cyclopentan-1-one;

2-(5-carboxypentyl)-3-(3-hydroxypent-1-enyl)cyclopentan-1-one, 2-(5-carboxypentyl)-3-(3-hydroxyhex-1-enyl)cyclopentan-1-one, 2-(5-carboxypentyl)-3-(3-hydroxyhept-1-enyl)cyclopentan-1-one, 2-(5-carboxypentyl)-3-(3-hydroxyoct-1-enyl)cyclopentan-1-one, 2-(5-carboxypentyl)-3-(3-hydroxynon-1-enyl)cyclopentan-1-one, and 2-)5-carboxypentyl)-3-(3-hydroxydec-1-enyl)cyclopentan-1-one;

2-(7-carboxyheptyl)-3-(3-hydroxypent-1-enyl)cyclopentan-1-one, 2-(7-carboxyheptyl)-3-(3-hydroxyhex-1-enyl)cyclopentan-1-one, 2-(7-carboxyheptyl)-3-(3-hydroxyhept-1-enyl)cyclopentan-1-one, 2-(7-carboxyheptyl)-3-(3-hydroxyoct-1-enyl)cyclopentan-1-one, 2-(7-carboxyheptyl)-3-(3-hydroxynon-1-enyl)cyclopentan-1-one, and 2-(7-carboxyheptyl)-3-(3-hydroxydex-1-enyl)cyclopentan-1-one;

2-(5-carboxypent-2-enyl)-3-(3-hydroxypent-1-enyl)cyclopentan-1-one, 2-(5-carboxypent-2-enyl)-3-(3-hydroxyhex-1-enyl)cyclopentan-1-one, 2-(5-carboxypent-2-enyl)-3-(3-hydroxyhept-1-enyl)cyclopentan-1-one, 2-(5-carboxypent-2-enyl)-3-(3-hydroxyoct-1-enyl)cyclopentan-1-one, 2-(5-carboxypent-2-enyl)-3-(3-hydroxynon-1-enyl)cyclopentan-1-one, and 2-(5-carboxypent-2-enyl)-3-(3-hydroxydec-1-enyl)cyclopentan-1-one;

2-(6-carboxyhex-2-enyl)-3-(3-hydroxypent-1-enyl)cyclopentan-1-one, 2-(6-carboxyhex-2-eryl)-3-(3-hydroxyhex-1-enyl)cyclopentan-1-one, 2-(6-carboxyhex-2-enyl)-3-(3-hydroxyhept-1-enyl)cyclopentan-1-one, 2-(6-carboxyhex-2-enyl)-3-(3-hydroxyoct-1-enyl)cyclopentan-1-one, 2-(6-carboxyhex-2-enyl)-3-(3-hydroxynon-1-enyl)cyclopentan-1-one, and 2-(6-carboxyhex-2-enyl)-3-(3-hydroxydex-1-enyl)cyclopentan-1-one;

2-(7-carboxyhept-2-enyl)-3-(3-hydroxypent-1-enyl)cyclopentan-1-one, 2-(7-carboxyhept-2-enyl)-3-(3-hydroxyhex-1-enyl)cyclopentan-1-one, 2-(7-carboxyhept-2-enyl)-3-(3-hydroxyhept-1-enyl)cyclopentan-1-one, 2-(7-carboxyhept-2-enyl)-3-(3-hydroxyoct-1-enyl)cyclopentan-1-one, 2-(7-carboxyhept-2-enyl)-3-(3-hydroxynon-1-enyl)cyclopentan-1-one, and 2-(7-carboxyhept-2-enyl)-3-(3-hydroxydec-1-enyl)cyclopentan-1-one;

2-(5-carboxypent-2-ynyl)-3-(3-hydroxypent-1-enyl)cyclopentan-1-one, 2-(5-carboxypent-2-ynyl)-3-(3-hydroxyhex-1-enyl)cyclopentan-1-one, 2-(5-carboxypent-2-ynyl)-3-(3-hydroxyhept-1-enyl)cyclopentan-1-one, 2-(5-carboxypent-2-ynyl)-3-(3-hydroxyoct-1-enyl)cyclopentan-1-one, 2-(5-carboxypent-2-ynyl)-3-(3-hydroxynon-1-enyl)cyclopentan-1-one, and 2-(5-carboxypent-2-ynyl)-3-(3-hydroxydec-1-enyl)cyclopentan-1-one;

2-(6-carboxyhex-2-ynyl)-3-(3-hydroxypent-1-enyl)cyclopentan-1-one,
2-(6-carboxyhex-2-ynyl)-3-(3-hydroxyhex-1-enyl)cyclopentan-1-one,
2-(6-carboxyhex-2-ynyl)-3-(3-hydroxyhept-1-enyl)cyclopentan-1-one,
2-(6-carboxyhex-2-ynyl)-3-(3-hydroxyoct-1-enyl)cyclopentan-1-one,
2-(6-carboxyhex-2-ynyl)-3-(3-hydroxynon-1-enyl)cyclopentan-1-one, and
2-(6-carboxyhex-2-ynyl)-3-(3-hydroxydex-1-enyl)cyclopentan-1-one; and
2-(7-carboxyhept-2-ynyl)-3-(3-hydroxypent-1-enyl)cyclopentan-1-one,
2-(7-carboxyhept-2-ynyl)-3-(3-hydroxyhex-1-enyl)cyclopentan-1-one,
2-)7-carboxyhept-2-ynyl)-3-(3-hydroxyhept-1-enyl)cyclopentan-1-one,
2-(7-carboxyhept-2-ynyl)-3-(3-hydroxyoct-1-enyl)cyclopentan-1-one,
2-(7-carboxyhept-2-ynyl)-3-(3-hydroxynon-1-enyl)cyclopentan-1-one, and
2-(7-carboxyhept-2-ynyl)-3-(3-hydroxydex-1-enyl)cyclopentan-1-one, are obtained, respectively.

2-(6-Carboxyhex-2-enyl)-3-(3-hydroxyoct-1-enyl)cyclopentan-1-one methyl ester had $\gamma_{max}^{Film}$ 3475,1735, cm$^{-1}$.

2-(6-Carboxyhex-2-ynyl)-3-(3-hydroxyoct-1-enyl)cyclopentan-1-one methyl ester has $\gamma_{max}^{Film}$ 3500, 1736, cm$^{-1}$.

Hydrolysis of the lower alkyl esters, described herein, to their corresponding acids is readily effected by treating the ester with an aqueous solution of an alkali metal hydroxide in lower alkanol solution, for example 10% aqueous sodium hydroxide in methanol, from 6 to 12 hours at room temperature. neutralizing the solution with hydrochloric acid and extraction with ether.

EXAMPLE 6

A solution of 2-(6-carboxyhexyl)-3-nitromethylcyclopentan-1-one methyl ester (20 g) in sodium hydroxide (10%, 61.6 ml) and methanol (40 ml) is stirred overnight, dilited with water (140 ml), and added to a mixture of concentrated sulfuric acid (18.4 ml) and water (118 ml) maintained −5° to −10° . A small amount of ether is added to keep the compound well suspended in the liquid. After completion of addition the cooling bath is removed and the mixture is stirred for 1 hour, extracted with ether, washed, dried and evaporated under reduced pressure to give a residue containing 2-(6-carboxyhexyl)cyclopentan-1-on-3-al $\gamma_{max}^{Film}$ 2700, 1730 cm$^{-1}$. This residue is refluxed in methanol (120 ml) containing p-toluenesulfonic acid (3 g) for 1.5 to 2 hours, the solvent evaporated, and the residue extracted with ether, washed with water, dried and evaporated to yield a residue which is passed through silica gel (1 kg) in 20% acetone-hexane to yield the methyl ester of 2-(6-carboxyhexyl)cyclopentan-1-on-3-al dimethyl acetal $\gamma_{max}^{Film}$ 1730, 1124, 1072 cm$^{-1}$ NMR: (CDCl$_3$) 4.25, 3.63, 3.38$\delta$.

In the same manner, the ethyl, methyl, propyl, isopropyl, n-butyl, n-pentyl, or n-hexyl esters of 2-(6-carboxyhexyl)3-nitromethyl-cyclopentan-1-one give 2-(6-carboxyhexyl) cyclopentan-1-on-3-al, and treatment of the latter compound with ethanol, propanol, isopropanol, n-butanol, n-pentanol, or n-hexanol yields the corresponding ethyl, propyl, isopropyl, n-butyl, n-pentyl, and n-hexyl esters of 2-(6-carboxyhexyl)cyclopentan-1-on-3-al diethyl, dipropyl, diisopropyl, di-n-butyl, di-n-pentyl, and di-n-hexyl acetal, respectively.

In the same manner the methyl, ethyl, propyl, isopropyl, n-butyl, n-pentyl and n-hexyl esters of
2-(5-carboxypentyl)-3-nitrometyl-cyclopentan-1-one,
2-(7-carboxyheptyl-3-nitrometyl-cyclopentan-1-one,
2-(5-carboxypent-2-enyl)-3-nitrometyl-cyclopentan-1-one,
2-(6-carboxyhex-2-enyl)-3-nitrometyl-cyclopentan-1-one, 2-(7-carboxyhept-2-enyl)-3-nitromethyl-cyclopentan-1-one,
2-(5-carboxypent-2-ynyl)-3-nitromethyl-cyclopentan-1-one, 2-(6-carboxyhex-2-ynyl)-3-nitrometyl-cyclopentan-1-one, and
2-(7-carboxyhept-2-ynyl)-3-nitrometyl-cyclopentan-1-one, obtained as described in Example 1, yield the corresponding 3-aldehyde derivatives of formula IV, which on treatment with methanol, ethanol, propanol, isopropanol, n-butanol, n-pentanol or n-hexanol yields the corresponding methyl, ethyl, propyl, isopropyol, n-butyl, n-pentyl and n-hexyl esters of
2-(5-carboxypentyl)cyclopentan-1-on-3-al,
2-(7-carboxyheptyl)cyclopentan-1-on-3-al,
2-(5-carboxypent-2-enyl)cyclopentan-1-on-3-al,
2-(6-carboxyhex-2-enyl)cyclopentan-1-on-3-al,
2-(7-carboxhept-2-enyl)cyclopentan-1-on-3-al,
2-(5-carboxypent-2-ynyl)cyclopentan-1-on-3-al,
2-(6-carboxyhex-2-ynyl)cyclopentan-1on-3al, and
2-(7-carboxyhept-2-ynyl)cyclopentan-1on-3-al dimethyl, diethyl, dipropyl, diisopropyl, di-n-butyl, di-n-pentyl and di-n-hexyl acetal, respectively.

EXAMPLE 7

To a solution of the methyl ester of 2-(6-carboxyhexyl)-cyclopentan-1-on-3-al dimethyl acetal (3.0 g), obtained as described in Example 6, in methanol (30 ml), sodium borohydride(0.375 g) is added keeping the solution in ice water during the addition. After stirring for 10 minutes the mixture is diluted with ether (160 ml) and with saturated ammonium chloride, the ether phase washed with saturated sodium chloride solution, dried, and evaporated to give a residue containing the methyl ester of 2-(6-carboxyhexyl)-cyclopentan-1-ol-3-al dimethyl acetal.

The above residue is stirred in tetrahydrofuran (3 ml) containing 25% sulfuric (0.3 ml), for a period of 2 hours at room temperature. The reaction mixture is diluted with ether, washed with water, dried, and the solvent evaporated to yield a residue containing the methyl ester of 2-(6-carboxyhexyl)cyclopentan-1-ol-3-al, $\gamma_{max}$ 2700 cm$^{-1}$.

The above residue (2.8 g) is dissolved in methylene chloride (17 ml) and dihydropyran (7 ml) and p-toluenesulfonic acid (19 mg) is added. The mixture is stirred at room temperature for 1 hour, diluted with methylene chloride, washed with water, dried and the solvent evaporated. The residue is chromatographed on silica gel (200 g) in 20% acetone-hexane to yield the methyl ester of 2-(6-carboxyhexyl)-2-tetrahydropyranyloxy-cyclopentan-3-al; $\gamma_{max}^{Film}$ 2700, 1735, 1715, 1127, 1112, 1075, 1027, 1020 cm$^{-1}$, NMR: (CDCl$_3$) 9.68, 4.68, 4.33-3.2 $\delta$ In the same manner the ethyl, propyl, isopropyl, n-butyl, n-pentyl, or n-hexyl esters of 2-(6-carboxyhexyl)-cyclopentan-1-on-3-al diethyl, dipropyl, diisopropyl, di-n-butyl, di-n-pentyl, or di-n-hexyl acetal, obtained as described in Example 6, yield the ethyl, propyl, isopropyl, n-butyl, n-pentyl, and n-hexyl esters of 2-(6-carboxyhexyl)-1-tetrahydropyranyloxy-cyclopentan-3-al, respectively.

In the same manner the methyl, ethyl, propyl, isopropyl, n-butyl, n-pentyl and n-hexyl esters of
2-(5-carboxypentyl)cyclopentan-1-on-3-al,
2-(7-carboxyheptyl)cyclopentan-1-on-3-al,
2-(5-carboxypent-2-enyl)cyclopentan-1-on-3-al,
2-(6-carboxyhex-2-enyl)cyclopentan-1-on-3-al,
2-(7-carboxyhept-2-enyl)cyclopentan-1-on-3-al,
2-(5-carboxypent-2-ynyl)cyclopentan-1pn-3-al,
2-(6-carboxyhex-2-ynyl)cyclopentan-1-on-3al, and
2-(7carboxyhept-2-ynyl)cyclopentan-1-on-3-al dimethyl, diethyl, dipropyl, diisopropyl, di-n-butyl, di-n-pentyl, or di-n-hexyl acetal, obtained as described in Example 6 yield the methyl, ethyl, propyl, isopropyl, n-butyl n-pentyl, n-hexyl esters of
2-(5-carboxypentyl)-1-tetrahydropyranyloxy-cyclopentan-3-al,
2-(7-carboxyheptyl)-1-tetrahydropyranyloxy-cyclopentan-3-al,
2-(5-carboxypent-2-enyl)-1-tetrahydropyranyloxy-cyclopentan-3al,
2-(6-carboxyhex-2-enyl)-1-tetrahydropyranyloxy-cyclopentan-3al,
2-(7-carboxyhept-2-enyl)-1-tetrahydropyranyloxy-cyclopentan-b 3al,
2-(5-carboxypent-2-ynyl-1-tetrahydropyranyloxy-cyclopentan-3-al,
2-(6-carboxyhex-2-ynyl)-1-tetrahydropyranyloxy-cyclopentan-3al, and
2-(7-carboxyhept-2-ynyl)-1-tetrahydropyranyloxy-cyclopentan-3al.

EXAMPLE 8

To a solution of the methyl ester of 2-(6-carboxyhexyl)-3-nitromethyl-cyclopentan-1-one (27 g), obtained as previously described in Example 1, in methanol (140 ml), sodium borohydride (1.24 g) is added with cooling in an ice bath during addition. The mixture is stirred for 30 minutes, acetic acid (1.4 ml) is added and the methanol is evaporated. The residue is taken in ether, washed with water, dried, and the solvent evaporated to yield the methyl ester of 2-(6-carboxyhexyl)-3-nitromethyl-cyclopentan-1-ol, $\gamma_{max}^{Film}$ 3440, 1725, 1549 cm$^{-1}$, NMR: 4.4, 3.69 δ.

In the same manner the ethyl, propyl, isopropyl, n-butyl, n-pentyl, or n-hexyl esters of 2-(6-carboxyhexyl)-3-nitromethyl-cyclopentan-1-one, obtained as described in Example 1, yield the ethyl, propyl, isopropyl, n-butyl, n-pentyl, and n-hexyl esters of 2-(6-carboxyhexyl)-3-nitromethyl-cyclopentan-1-ol.

In the same manner the methyl, ethyl, propyl, isopropyl, n-butyl, n-pentyl or n-hexyl esters of
2-(5-carboxypentyl)-3-nitromethyl-cyclopentan-1-one,
2-(7-carboxyheptyl)-3-nitromethyl-cyclopentan-one,
2-(5-carboxypent-2-enyl)-3-(3-nitromethyl-cyclopentan-1-one, 2-(6-carboxyhex-2-enyl)-3-nitromethyl-cyclopentan-1-one,
2-(7-carboxyhept-2-enyl)-3-nitromethyl-cyclopentan-1-one
2-(5-carboxypent-2-ynyl)-3-nitromethyl-cyclopentan-1-one,
2-(6-carboxyhex-2-ynyl)-3-nitromethyl-cyclopentan-1-one, and
2-(7-carboxyhept-2-ynyl)-3-nitromethyl-cyclopentan-1-one obtained as described in Example 1, yield the methyl, ethyl, propyl, isopropyl, n-butyl, n-pentyl and n-hexyl esters of
2-(5-carboxypentyl)-3-nitromethyl-cyclopentan-1-ol,
2-(7-carboxyheptyl)-3-nitromethyl-cyclopentan-1-ol,
2-(5-carboxypent-2-enyl)-3-nitromethyl-cyclopentan-1ol,
2-(6-carboxyhex-2-enyl)-3-nitromethyl-cyclopentan-1ol,
2-(7-carboxyhept-2-enyl)-3-nitromethyl-cyclopentan-1-ol,
2-(5-carboxypent-2-ynyl)-3nitromethyl-cyclopentan-1-ol,
2-(6-carboxyhex-2-ynyl)-3-nitromethyl-cyclopentan-1ol, and
2-(7-carboxyhept-2-ynyl)-3-nitromethyl-cyclopentan-1ol.

2-(6-Carboxyhex-2-enyl)-3-nitromethyl-cyclopentan-1-ol methyl ester has $\gamma_{max}^{Film}$ 3450, 1730, 1550 cm$^{-1}$.
2-(6-Carboxyhex-2-ynyl)-3-nitromethyl-cyclopentan-1ol methyl ester has $\gamma_{max}^{Film}$ 3400, 1735, 1550 cm$^{-1}$.

EXAMPLE 9

The methyl ester of 2-(6-carboxyhexyl)-3-nitromethyl-cyclopentan-1-ol (26.5 g) is dissolved in methanol (101 ml) containing sodium methoxide (1.2 eqvs., 2.56 g Na) and the solution is added to cold (0° to −10° C.) aqueous sulfuric acid (118.4 ml concentrated sulfuric acid and 739 ml water). The addition is carried out over 45 – 60 minutes at −5° to 9° C., the reaction mixture stirred for about 30 minutes after completion of addition and then allowed to come to room temperature. Extraction with ether washing with water, drying and evaporation of the solvent gives a residue containing the methyl ester of 2-(6-carboxyhexyl)cyclopentan-1-ol-3-al.

The above residue (22.3 g) is dissolved in methylene chloride (120 ml), dihydropyran (9.8 g) and p-toluenesulfonic acid (0.15 g) is added, the reaction mixture stirred for about 1 hour, diluted with about an equal volume of methylene chloride, washed with water several times, dried, and the solvent evaporated. The residue is passed through a column of silica gel (800 g) in 10% acetone-hexane and elution with the same solvent yields the methyl ester of 2-(6-carboxyhexyl)-1-tetrahydropyranyloxy-cyclopentan-3-al, identical with the same compound obtained as described in Example 7.

In the same manner the ethyl, propyl, isopropyl, n-butyl, n-pentyl, and n-hexyl esters of 2-(6-carboxyhexyl)-3-nitromethyl-cyclopenta-1-ol obtained as described in Example 8 yield the same ethyl, propyl, isopropyl, n-butyl, n-pentyl, and n-hexyl esters of 2-(6-carboxyhexyl)-1-tetrahydropyranyloxy-cyciopentan-3-al obtained as described in Example 7.

In the same manner the methyl, ethyl, propyl, isopropyl, n-butyl, n-pentyl and n-hexyl esters of
2-(5-carboxypentyl)-3-nitromethyl-cyclopentan-1-ol,
2-(7-carboxyheptyl)-3-nitromethyl-cyclopentan-1ol,
2-(5-carboxypent-2-enyl)-3-nitromethyl-cyclopentan-1-ol,
2-(6-carboxyhex-2-enyl)-3-nitromethyl-cyclopentan-1ol,
2-(7-carboxyhept-2-enyl)-3-nitromethyl-cyclopentan-1ol,
2-(5-carboxypent-2-ynyl)-3-nitromethyl-cyclopentan-1ol,
2-(6-carboxyhex-2-ynyl)-3-nitromethyl-cyclopentan-1-ol, and
2-(7-carboxyhept-2-ynyl)-3-nitromethyl-cyclopentan-1ol, obtained as described in Example 8, yield the methyl, ethyl, propyl, isopropyl, n-butyl, n-pentyl and n-hexyl esters of 2-(5-carboxypentyl)-1-tetrahydropyranyloxy-cyclopentan-3al, 2-(7-carboxyheptyl)-1-tetrahydropyranyloxy-cyclopentan-3-al, 2-(5-carboxypent-2-enyl)-1-tetrahydropyranyloxy-cyclopentan-3al, 2-(6-carboxyhex-2-enyl)-1-tetrahydropyranyloxy-cyclopentan-3-al, 2-(7-carboxyhept-2-enyl)-1-tetrahydropypyranyloxy-cyclopentan-3al, 2-(5-carboxypent-2-ynyl)-1-tetrahydropyranyloxy-cyclopentan-3al, 2-(6-carboxyhex-2-ynyl)-1-tetrahydropyranyloxy-cyclopentan-3al, and 2-(7-carboxyhept-2-ynyl)-1-tetrahydropyranyloxy-cyclopentan-3-al identical to the products of the same name described in Example 7.

2-(6-Carboxyhex-2-enyl)-1-tetrahydropyranyloxy-cyclopentan-3-al methyl ester has $\gamma_{max}{}^{Film}$ 1735, 1725 cm$^{-1}$.

2-(6-Carboxyhex-2-ynyl)-1-tetrahydropyranyloxy-cyclopentan-3-al methyl ester has $\gamma_{max}{}^{Film}$ 1736, 1725 cm$^{-1}$.

EXAMPLE 10

To a suspension of sodium hydride (1.48 g, 53% suspension) in dry dimethoxyethane (150 ml) a solution of dimethyl 2-oxoheptylphosphonate (7.6 g) in dry dimethoxyethane (150 ml) is added. The mixture is stirred at room temperature for 45 minutes, and a solution of the methyl ester of 2-(6-carboxyhexyl)-1-tetrahydropyranyloxy-cyclopentan-3-al (10,.5 g) in dimetoxyethane (150 ml) is added. The mixture is heated to about 60° C. bath temperature for 30 minutes, cooled, and 50% acetic acid (3 ml) is added. The mixture is diluted with ether, washed with water, dried and the solvent evaporated to yield a residue which is chramotographed on silica gel (750 g) from 7% ethyl acetate in benzene to yield the tetrahydropyranyl ether of 9-hydroxy-15-oxoprost-13-enoic acid methyl ester, $\gamma_{max}{}^{Film}$ 1735, 1670, 1620 cm$^{-1}$, NMR: (CDCl$_3$) 6.83, 6.02, 4.62, 4.12 - 3.45, 0.88 $\delta$ identical with the same compound described in British Patent No. 1,218,998 cited above.

In the same manner the ethyl, propyl, isopropyl, n-butyl, n-pentyl, or n-hexyl esters of 2-(6-carboxyhexy)-1-tetrahydropyranyloxy-cyclopentan-3-al give the tetrahydropyranyl ethers of 9-hydroxy-15-oxoprost-13-enoic acid ethyl, propyl, isopropyl, n-butyl, n-pentyl, and n-hexyl esters, respectively.

Again in the same manner, but using as starting materials the dimethyl 2-oxobutyl-, 2-oxopentyl-, 2-oxohexyl-, 2-oxooctyl-, or 2-oxononyl-phosphonates and reacting them with the methyl, ethyl, propyl, isopropyol, n-butyl, n-pentyl, or n-hexyl esters of 2-(6-carboxyhexyl)-1-tetrahydropyranyloxy-cyclopentan-3-al there are obtained the tetrahydropyranyl ethers of 2-(6-carboxyhexyl)-3-(3-oxopent-1-enyl)-cyclopentan-1ol, 2-(6-carboxyhexyl)-3-(3oxohex-1-enyl)-cyclopentan-1ol, 2-(6-carboxyhexyl)-3-(3-oxohept-1-enyl)-cyclopentan-1ol, 2-(6carboxyhexyl)-3-(3-oxonon-1enyl)-cyclopentan-1ol, and 2-(6-carboxyhexyl)-3-(3-oxodec-1-enyl)-cyclopentan-1ol methyl, ethyl, propyl, isopropyl, n-butyl, n-pentyl, and n-hexyl esters, respectively.

Again in the same manner, but using as starting material the Wittig reagents, dimethyl 2-oxobutyl-, 2-oxopentyl-, 2-oxohexyl-, 2-oxoheptyl-, 2-oxooctyl-, or 2-oxononyl-phosphonates and reacting them with the methyl, ethyl, propyl, isopropyl, n-butyl, n-pentyl, or n-hexyl esters of 2-(5-carboxypentyl)-1-tetrahydropyranyloxy-cyclopentan-3al there are obtained the tetrahydropyranyl ethers of 2-(5-carboxypentyl)-3-(3-oxopent-1-enyl)cyclopentan-1ol, 2-(5-carboxypenyl)-3-(3-oxohex-1-enyl) cyclopentan-1-ol, 2-)5-carboxypentyl)-3-(3-oxohept-1-enyl)cyclopentan-1ol, 2-(5-carboxypentyl)-3-(3-oxooct-1-enyl)cyclopentan-1ol, 2-(5-carboxypentyl)-3-(3-oxonon-1-enyl)cyclopentan-1-ol, and 2-(5-carboxypentyl)-3-(3-oxodec-1-enyl)ccyclopentan-1-ol methyl, ethyl, propyl, isopropyl, n-butyl, n-pentyl, and n-hexyl esters, respectively.

Again in the same manner, but using as starting material the preceding, respective Wittig reagents and reacting them with the methyl, ethyl, propyl, isopropyl, n-butyl, n-pentyl, or n-hexyl esters of 2-(7-carboxyheptyl)-1-tetrahydropyranyloxy-cyclopentan-3-al there are obtained the tetrahydropyranyl ethers of 2-(7-carboxyheptyl)-3-(3-oxopent-1-enyl)cyclopentan-1-ol, 2-(7-carboxyheptyl)-3-(3-oxohex-1-enyl)cyclopentan-1-ol, 2-(7-carboxyheptyl)-3-(3-oxohept-1-enyl)cyclopentan-1-ol, 2-(7-carboxyheptyl)-3-(3-oxooct-1-enyl)cyclopentan-1-ol, 2-(7-carboxyheptyl)-3-(3-oxonon-1-enyl)cyclopentan-1-ol, and 2-(7-carboxyheptyl)-3-(3-oxodec-1enyl)cyclopentan-1-ol methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl, esters of 2-(5-carboxypent-2-enyl- 1-tetrahydropyranloxy-cyclopentan-3-al there are obtained the tetrahydropyranyl ethers of 2-(5-carboxypent-2-enyl)-3-(3-oxopent-1-enyl)cyclopentan-1-ol, 2-(5-carboxypent-2enyl)-3-(3-oxohex-1-enyl)cyclopentan-1-ol, 2-(5-carboxypent-2-enyl)-3-(3-oxohept-1-enyl)cyclopentan-1-ol, 2-(5-carboxypent-2-enyl)-3-(3-oxooct-1enyl)cyclopentan-1-ol, 2-(5-carboxypent-2enyl)-3-(3-oxonon-1-enyl)cyclopentan-1-ol, and 2-(5-carboxypent-2enyl)-3(3oxodec-1enyl)cyclopentan-1-ol methyl, ethyl, propyl, isopropyl, n-butyl, n-pentyl, and n-hexyl esters, respectively.

Again in the same manner, but using as starting material the preceding respective Wittig reagents and reacting them with the methyl, eythyl, propyl, isopropyl, n-butyl, n-pentyl, or n-hexyl esters of 2-(6-carboxyhex- 2-enyl)-1tetrahydropyranyloxy-cyclopentan-3al there are obtained the tetrahydropyranyl ethers of
2-(6-carboxyhex-2-enyl)-3-(3-oxopent-1-enyl)cyclopentan-1-ol,
2-(6-carboxyhex-2-enyl)-3-(3-oxohex-1-enyl)cyclopentan-1-ol,
2-(6-carboxyhex-2-enyl)-3-(3-oxohept-1-enyl)cyclopentan-1-ol,
2-(6-carboxyhex-2-enyl)-3-(3-oxooct-1-enyl)cyclopentan-1-ol,
2-(6-carboxyhex-2-enyl)-3-(3-oxonon-1-enyl)cyclopentan-1-ol, and
2-(6-carboxyhex-2-enyl)-3-(3-oxodec-1-enyl)cyclopentan-1-ol methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl esters of 2-(7-carboxyhept-2-enyl)-1-tetrahydropyranyloxy-cyclopentan-3al there are obtained the tetrahydropyranyl ethers of
2-(7-carboxyhept-2-enyl)-3-(3-oxopent-1-enyl)cyclopentan-1-ol,
2-(7-carboxyhept-2-enyl)-3-(3oxohex-1-enyl)cyclopentan-1-ol,
2-(7-carboxyhept-2-enyl)-3-(3-oxohept-1-enyl)cyclopentan-1-ol,
2-(7-carboxyhept-2-enyl)-3-(3-oxooct-1-enyl)cyclopentan-1-ol,
2-(7-carboxyhept-2-enyl)-3-(3-oxonon-1-enyl)cyclopentan-1-ol, and
2-(7-carboxyhept-2-enyl)-3-(3-oxodec-1-enyl)cyclopentan-1-ol methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl esters of 2-(5-carboxypent-2-ynyl)-1-tetrahydropyranyloxy-cyclopentan-3-al there are obtained the tetrahydropyranyl ethers of
2-(5-carboxypent-2-ynyl)-3-(3-oxopent-1-enyl)cyclopentan-1-ol,
2-(5-carboxypent-2-ynyl)-3-(3-oxohex-1-enyl)cyclopentan-1-ol,
2-(5-carboxypent-2-ynyl)-3-(3-oxohept-1-enyl)cyclopentan-1-ol,
2-(5-carboxypent-2-ynyl)-3-(3-oxooct-1-enyl)cyclopentan-1-ol,
2-(5carboxypent-2-ynyl)-3-(3-oxonon-1-enyl)cyclopentan-1-ol, and
2-(5-carboxypent-2-ynyl)-3-(3-oxodec-1-enyl)cyclopentan-1-ol, methyl, ethyl, propyl, isopropyl, n-butyl, n-pentyl, and n-hexyl esters, respectively.

Again in the same manner, but using as starting material the preceding respective Wittig reagents and reacting them with the methyl, ethyl, propyl, isopropyl, n-butyl, n-pentyl, or n-hexyl esters of 2-(6-carboxyhex-2-ynyl)-1-tetrahydropyranyloxy-cyclopentan-3-al there are obtained the tetrahydropyranyl ethers of
2-(6-carboxyhex-2-ynyl)-3-(3-oxopent-1-enyl)cyclopentan-1-ol,
2-(6-carboxyhex-2-ynyl)-3-(3-oxohex-1-enyl)cyclopentan-1-ol,
2-(6-carboxyhex-2-ynyl)-3-(3-oxohept-1-enyl)cyclopentan-1-ol,
2-(6-carboxyhex-2-ynyl)-3-(3-oxooct-1-enyl)cyclopentan-1-ol,
2-(6-carboxyhex-2-ynyl)-3-(3-oxonon-1-enyl)cyclopentan-1-ol, and
2-(6-carboxyhex-2-ynyl)-3-(3-oxodec-1-enyl)cyclopentan-1-ol, methyl, ethyl, propyl, isopropyl, n-butyl, n-pentyl, and n-hexyl esters, respectively.

Again in the same manner, but using as starting material of the preceding respective Wittig reagents and reacting them with the methyl, ethyl, propyl, isopropyl, n-butyl, n-pentyl, or n-hexyl esters of 2-(7-carboxyhept-2-ynyl)-1-tetrahydropyranyloxy-cyclopentan-3-al there are obtained the tetrahydropyranyl ethers of
2-(7-carboxyhept-2-ynyl)-3-(3-oxopent-1-enyl)cyclopentan-1-ol,
2-(7-carboxyhept-2-ynyl)-3-(3-oxohex-1-enyl)cyclopentan-1ol,
2-(7-carboxyhept-2-ynyl)-3-(3-oxohept-1-enyl)cyclopentan-1-ol,
2-(7-carboxyhept-2-ynyl)-3-oxooct-1-enyl)cyclopentan-1-ol,
2-(7-carboxyhept-2-ynyl)-3-(3-oxonon-1-enyl)cyclopentan-1-ol, and
2-(7-carboxyhept-2-ynyl)-3-(3-oxodec-1-enyl)cyclopentan-1-ol, methyl, ethyl, propyl, isopropyl, n-butyl, n-pentyl, and n-hexyl esters, respectively.

The tetrahydropyranyl ether of 2-(6-carboxyhex-2-enyl)-3-(3-oxooct-1-enyl)cyclopentan-1-ol methyl ester has $\gamma_{max}^{Film}$ 3450, 1735, 1670, 1625 cm$^{-1}$, NMR; (CDCl$_3$) 6.7, 6.1, 5.5, 4.7, 3.7, 0.95 δ.

EXAMPLE 11

By following the procedure of A.I. Rachlin, et al., cited above, 6-chloro-2-hexyn-1-ol is prepared by condensing propargyl alcohol tetrahydropyran-2-yl ether and the dihaloalkane, 1-bromo-3-chloropropane, to give 1-[(tetrahydropyran-2-yl)oxy]-6-chloro-2-hexyne, which is then converted to the desired compound followed by hydrolysis in the presence of sulfuric acid. The 6-chloro2-hexyl-1-ol (280 g) is dissolved in ethanol (2.8 l) then water (560 ml) and potassium cyanide (290 g) is added and the mixture stirred and refluxed for 20 hr. Potassium hydroxide (768 g) and water (500 ml) are added and the stirred mixture kept at reflux for an additional 20 hr. Methanol is evaporated and the water phase is acidified with concentrated HCl and extracted with ether for 2 days in a continuous liquid-liquid extractor. The ether extract is dried (Na$_2$SO$_4$) and concentrated to give 7-hydroxy-5-heptynoic acid, NMR: (CDCl$_3$) 4.22 (m, 2H), 7.41 (broad, 2H) δ.

EXAMPLE 12

To a solution of 7-hydroxy-5-heptynoic acid (88.2 g), described in Example 11, in anhydrous ether (300 ml) and pyridine (12 ml) is added dropwise phosphorus tribromide (67.5 g) at 10° C. The solution is stirred at room temperature for 30 min. then cooled to 5° C and 10% HCl (120 ml) is added slowly. The organic layer is washed with water and 10% sodium carbonate, dried (Na$_2$SO$_4$) and concentrated. The residue is distilled under reduced pressure to give 7-bromo-5-heptynoic acid, b.p. 146° C, 0.8 mm.

The latter compound is esterified in the following manner. The latter compound (156 g) is dissolved in absolute methanol (1.5 l). p-Toluenesulfonic acid (78 g) is added to the solution which is then heated at reflux for 2 hr. Thereafter the solvent is evaporated. The residue is dissolved in water and the aqueous solution extracted with benzene. The extract is washed with 10% Na$_2$CO$_3$ and then water until neutral, dried (Na$_2$SO$_4$)

and concentrated. The residue is distilled to give methyl 7-bromo-5-heptynoate, b.p. 70°–80° C, 0.2 mm.

The corresponding ethyl or other lower alkyl esters of the latter compound are likewise prepared according to the preceding esterification procedure by replacing methanol with ethanol or an appropriate corresponding lower alkanol, respectively.

Alternatively, the procedure of the example may be reversed whereby 7-hydroxy-5-heptynoic acid is first subjected to the esterification procedure with methanol and p-toluenesulfonic acid, followed by treatment of the resulting hydroxy ester with phosphorus tribromide as described herein.

By following serially the procedures of Examples 11 and 12 but using the dihaloalkanes, 1-bromo-2-chloroethane or 1-bromo-4-chlorobutane, instead of 1-bromo-4-chloropropane, then methyl 6-bromo-4-hexynoate and methyl 8-bromo-6-octynoate are obtained, respectively.

EXAMPLE 13

Sodium hydride (4.2 g) is suspended in dimethylformamide (50 ml) and while stirring the mixture at room temperature, a solution of 3,5-cyclohexanedione (11.2 g) in dimethylformamide (50 ml) is added over a period of 10 minutes. Several minutes later the mixture is cooled to −10° C., and a solution of methyl 7-bromo-5-heptynoate, described in Example 12, in dimethylformamide (50 ml) is added. The reaction mixture is stirred overnight at −10° to −5° C., then ether is added. The mixture is extracted with sodium carbonate. The aqueous extract after acidification with 10% HCl is extracted with ethyl acetate to yield a crude product, which on crystallization from ether affords 7-(2,6-dioxocyclohexyl)5-heptynoic acid methyl ester, m.p. 108° – 110° C, $\epsilon_{max}^{EtOH}$ 256nm ($\epsilon$ = 14,200).

In the same manner but using methyl 6-bromo-4-hexynoate or methyl 8-bromo-6-octynoate, instead of methyl 7-bromo-5-heptynoate, 6-(2,6-dioxocyclohexyl)-4-hexynoic acid methyl ester and 8-(2,6-dioxocyclohexyl)-6-octynoic acid methyl ester are obtained.

EXAMPLE 14

7-(2,6-Dioxocyclohexyl)-5-heptynoic acid methyl ester (21.0 g), prepared as described in Example 13, is dissolved in chloroform (300 ml) cooled to 20° C and t-butyl hypochlorite (9.5 g) in chloroform (10 ml) is added to the well stirred solution over a period of 15 minutes. The mixture is stirred for another 30 minutes and allowed to warm up to room temperature. Removal of the solvent affords 7-(1-chloro-2,6-dioxocyclohexyl)-5-heptynoic acid methyl ester, $\gamma_{max}^{Film}$ 1730, 1720.

In the same manner but using 6-(2,6-dioxocyclohexyl)-4-hexynoic acid methyl ester or 8-(2,6-dioxocyclohexyl)-6-octynoic acid methyl ester described in Example 13, instead of 7-(2,6-dioxocylohexyl)-5-heptynoic acid methyl ester, 6-(1-chloro-2,6-dioxocyclohexyl)-4-hexynoic acid methyl ester and 8-(1-chloro-2,6-dioxocyclohexyl)-6-octynoic acid methyl ester are obtained respectively.

EXAMPLE 15

To a solution of 7-(1-chloro-2,6-dioxocyclohexyl)-5-heptynoic acid methyl ester (23.6 g), described in Example 14, in xylene (250 ml) is added powdered sodium carbonate (11.8 g) and the mixture stirred and heated at reflux for 16 hr. After cooling the mixture is washed with water to neutral, dried over magnesium sulfate, and the solvent evaporated to give the crude cyclopentenone ester. Distillation of the crude ester at 0.6 mm Hg affords 7-(5-oxocyclopent-1-enyl)-5-heptynoic acid methyl ester, b.p. 142° – 156° C.

In the same manner but using 6-(1-chloro-2,6-dioxocyclohexyl)-4-hexynoic acid methyl ester or 8-(1-chloro-2,6-dioxocyclohexyl)-6-octynoic acid methyl ester instead of 7-(1-chloro-2,6-dioxocyclohexyl)-5-heptynoic acid methyl ester, 6-(5-oxocyclopent-1-enyl)-4-hexynoic acid methyl ester and 8-(5-oxocyclopent-1-enyl)-6octynoic acid methyl ester are obtained respectively.

EXAMPLE 16

A solution of 7-(5-oxocyclopent-1-enyl)-5-heptynoic acid methyl ester (8.13 g) in ethyl acetatehexane (5:100) (105 ml) is hydrogenated in the presence of Lindlar catalyst (1.5 g), at room temperature and atmospheric pressure. The mixture is filtered through diatomaceous earth ("Celite") and the filtrate evaporated to give 7-(5-oxocyclopent-1-enyl)-5-heptanoic acid methyl ester, $\gamma_{max}^{Film}$ 1735, 1700, 1640 cm$^{-1}$, NMR: (CDCl$_3$) 7.35, 5.5, 3.65 $\delta$.

In the same manner but using 6-(5-oxocyclopent-1-enyl)-4-hexynoic acid methyl ester or 8-(5-oxocyclopent-1-enyl)-6-octynoic acid methyl ester instead of 7-(5-oxocyclopent-1-enyl)-5-heptynoic acid methyl ester, 6-(5-oxocyclopent-1-enyl)-4-hexenoic acid methyl ester and 8-(5-oxocyclopent-1-enyl)-6-octenoic acid methyl ester are obtained, respectively.

EXAMPLE 17

Alternatively 6-(5-oxocyclopent-1-enyl)-4-hexenoic acid methyl ester, 7-(5-oxocyclopent-1-enyl)-5-heptenoic acid methyl ester and 8-(5-oxocyclopent-1-enyl)-6-octenoic acid methyl ester, as well as, 6-(5-oxocyclopent-1enyl)hexanoic acid methyl ester, 7-(5-oxocyclopent-1-enyl)heptanoic acid methyl ester, and 8-(5-oxocyclopent-1-enyl)octanoic methyl ester are prepared by following serially the procedures of Examples 13, 14 and 15, and using methyl 6-bromo-4-hexenoate, methyl 7-bromo-5-heptanoate, methyl 8-bromo-6-octenoate, methyl 6-bromohexanoate, methyl 7-bromoheptanoate, and methyl 8-bromooctanoate, respectively, as starting material instead of methyl 7-bromo-5-heptynoate.

EXAMPLE 18

By following the procedure described in British Pat. No. 1,218,988, cited above, for converting the tetrahydropyranyl ether of 9-hydroxy-15-oxoprost-13-enoic acid methyl ester, described herein in Example 10, to 15-hydroxy-9-oxoprost-13-enoic acid methyl ester, described here in Example 5, the tetrahydropyranyl ethers of formula XII, described herein in Example 10, may be converted to the respective compounds of formula XI, described herein in Example 5.

A specific exemplification of this conversion is given as follows:

To a solution of tetrahydropyranyl ether of 2-(6-carboxyhex-2-enyl)-3-(3-oxooct-1-enyl)cyclopentan-1-ol methyl ester (3.37 g), described in Example 10, in methanol, sodium borohydride (310 mg) is added at 0° C. The mixture is neutralized with acetic acid and the solvent evaporated. The residue is taken up in ether. The ether solution is washed with water, dried and evaporated to yield the 1-tetrahydropyranyl ether of 2-(6-carboxyhex-2-enyl)-3-(3-hydroxy-1-enyl)cyclopentan-1-ol methyl ester, i.e., the 9-tetrahydropyranyl ether of 9,15-dihydroxyprosta-5,13-dienoic acid methyl ester, $\gamma_{max}{}^{Film}$ 3500, 1740 cm$^{-1}$.

The latter compound (3.19 g) is dissolved in pyridine (4.5 ml) and acetic anhydride (8.4 ml). The solution is stirred at room temperature for one hour. Excess acetic anhydride is decomposed with methanol and then the reaction mixture is evaporated to dryness. The residue is dissolved in ether. The ether solution is washed with water, dried and concentrated to give the 1-tetrahydropyranyl ether of 2-(6-carboxyhex-2-enyl)-3-(3-acetoxyoct-1-enyl)cyclopentan-1-ol methyl ester, $\gamma_{max}{}^{Film}$ 3420, 1735 cm$^{-1}$.

To a solution of the latter compound (3.35 g) in tetrahydrofuran (3 ml), acetic acid (33 ml) and water (10 ml) is added. The mixture is stirred at 60° C for 16 hr. The solvent is removed under reduced pressure and the residue taken up in ether. The ether solution is washed with water, dried and evaporated to give 2-(6-carboxyhex-2-enyl)-3-(3-acetoxyoct-1-enyl)cyclopentan-1-ol methyl ster, $\gamma_{max}{}^{Film}$ 3500, 1735 cm$^{-1}$.

The latter compound (3.07 g) is dissolved in acetone (30 ml). The solution is cooled to 0° C. Jones reagent (3.5 ml), A. Bowers, et al., J. Chem. Soc., 2555 (1953), is added dropwise to the solution over 10 minutes. Methanol (20 ml) is then added and the solvent removed under reduced pressure. The residue is dissolved in ether. The ether solution is washed with water, dried and evaporated to yield 2-(6-carboxyhex-2-enyl)-3-(3-acetoxyoct-1-enyl)cyclopentan-1-one methyl ester, $\gamma_{max}{}^{Film}$ 1735 cm$^{-1}$.

To a solution of the latter compound (2.62 g) in methanol (30 ml), a solution of sodium methoxide (from 200 mg sodium) in methanol (20 ml) is added. The mixture is stirred for 2 hr. at room temperature. After the addition of acetic acid (7 drops), the solvent is evaporated and the residue taken up in ether. The ether solution is washed with water, dried and concentrated to give 15-hydroxy-9-oxoprosta-5,13-dienoic acid methyl ester, i.e. 2-(6-carboxyhex-2-enyl)-3-(3-hydroxyoct-1-enyl)cyclopentan-1-one methyl ester, identical to the product of the same name described in Example 5.

If desired the latter product may be separated into two isomers. These two isomers are epimeric alcohols resulting from the asymmetrical carbon atom to which the hydroxy group is attached in the side chain. For example separation of 2.4 g of the latter product is effected readily by chromatography on 300 g. of silica gel using ether-hexane (45:55) as eluant (50 ml fractions). Fractions 81 – 136 gives one isomer, designated isomer A, NMR: (CDCl$_3$) 5.6, 5.37, 4.1, 3.65, 0.9 $\gamma$, and fractions 156 – 210 give the other isomer, designated isomer B, NMR: (CDCl$_3$) 5.6, 5.37, 4.1, 3.65, 0.9 $\delta$.

The preceding two isomers may be distinguished from each other by their different Rf values (tlc) in the above etherhexane solvent system. In this case isomer A is the less polar.

Hydrolysis of the latter two isomers according to the procedure of Example 5 yields respectively, 2-(6-carboxyhex-2-enyl)-3-(3-hydroxyoct-1-enyl-cyclopentan-1-one (Isomer A), NMR: (CDCl$_3$) 5.6, 5.4, 4.15, 0.9$\delta$, and 2-(6-carboxyhex-2-enyl)-3-(3-hydroxyoct-1-enyl)cyclopentan-1-one (Isomer B), NMR: (CDCl$_3$) 5.65, 5.42, 4.15, 0.9 $\delta$.

EXAMPLE 19

By following the procedure of Example 7 but using as starting material, an equivalent amount of 9,15-dioxoprost-13-enoic acid methyl ester, described in Example 3, instead of the methyl ester of 2-(6-carboxyhexyl)cyclopentan-1-on-3-al dimethyl acetal, 9,15-dihydroxyprost-13-enoic acid methyl ester, identical to the same compound described in U.S. Pat. No. 3,432,541, is obtained.

In the same manner but using as starting material the ethyl, propyl, isopropyl, n-butyl, n-pentyl and n-hexyl esters of 9,15-dioxoprost-13-enoic acid, there are obtained the ethyl, propyl, isopropyl, n-butyl, n-pentyl and n-hexyl esters of 9,15-dihydroxyprost-13-enoic acid.

Again in the same manner, but using as starting materials the methyl, ethyl, propyl, isopropyl, n-butyl, n-pentyl, and n-hexyl esters of 2-(6-carboxyhexyl)-3-(3-oxopent-1-enyl)cyclopentan-1-one, 2-(6-carboxyhexyl)-3-(3-oxohex-1-enyl)cyclopentan-1-one, 2-(6-carboxyhexyl)-3-(3-oxohept-1-enyl)cyclopentan-1-one, 2-(6-carboxyhexyl)-3-(3-oxonon-1-enyl)cyclopentan-1-one, and 2-(6-carboxyhexyl)-3-(3-oxodec-1-enyl)cyclopentan-1-one, described in Example 3, there are obtained the methyl, ethyl, propyl, isopropyl, n-butyl, n-pentyl, nd n-hexyl esters of 2-(6-carboxyhexyl)-3-(3-hydroxypent-1-enyl)cyclopentan-1-ol, 2-(6-carboxyhexyl)-3-(3-hydroxyhex-1-enyl)cyclopentan-1-ol, 2-(6-carboxyhexyl)-3-(3-hydroxyhept-1-enyl)cyclopentan-1-ol, 2-(6-carboxyhexyl)-3-(3-hydroxynon-1-enyl)cyclopentan-1-ol, and 2-(6-carboxyhexyl)-3-(3-hydroxydec-1-enyl)cyclopentan-1-ol, respectively.

Again in the same manner, but using as starting materials the methyl, ethyl, propyl, isopropyl, n-butyl, n-pentyl or n-hexyl esters of 2-(5-carboxypentyl)-3-(3-oxopent-1-enyl)cyclopentan-1-one, 2-(5-carboxypentyl)-3-(3-oxohex-1-enyl)cyclopentan-1-one, 2-(5-carboxypentyl)-3-(3-oxohept-1-enyl)cyclopentan-1-one, 2-(5-carboxypentyl)-3-(3-oxooct-1-enyl)cyclopentan-1-one, 2-(5-carboxypentyl)-3-(3-oxonon-1-enyl)cyclopentan-1-one, and 2-(5-carboxypentyl)-3-(3-oxodec-1-enyl)cyclopentan-1-one, there are obtained the methyl, ethyl, propyl, isopropyl, n-butyl, n-pentyl, and n-hexyl esters of 2-(5-carboxypentyl)-3-(3-hydroxypent-1-enyl)cyclopentan-1-ol, 2-(5-carboxypentyl)-3-(3-hydroxyhex-1-enyl)cyclopentan-1-ol, 2-(5-carboxypentyl)-3-(3-hydroxyhept-1-enyl)cyclopentan-1-ol, 2-(5-carboxypentyl)-3-(3-hydroxyoct-1-enyl)cyclopentan-1ol, 2-(5-carboxypentyl)-3-(3-hydroxynon-1-enyl)cyclopentan-1-ol, and 2-(5-carboxypentyl)-3-(3-hydroxydec-1-enyl)cyclopentan-1-ol, respectively.

Again in the same manner, but using as starting materials, the methyl, ethyl, propyl, isopropyl, n-butyl, n-pentyl or n-hexyl esters of 2-(7-carboxyheptyl)-3-(3-oxopent-1-enyl)cyclopentan-1-one,
2-(7-carboxyheptyl)-3-(3-oxohex-1-enyl)cyclopentan-1-one,
2-(7-carboxyheptyl)-3-(3-oxohept-1-enyl)cyclopentan-1-one,
2-(7-carboxyheptyl)-3-(3-oxooct-1-enyl)cyclopentan-1-one,
2-(7-carboxyheptyl)-3-(3-oxonon-1-enyl)cyclopentan-1-one, and
2-(7-carboxyheptyl)-3-(3-oxodec-1-enyl)cyclopentan-1-one, there are obtained the methyl, ethyl, propyl, isopropyl, n-butyl, n-pentyl, and n-hexyl esters of
2-(7-carboxyheptyl)-3-(3-hydroxypent-1-enyl)cyclopentan-1-ol,
2-(7-carboxyheptyl)-3-(3-hydroxyhex-1-enyl)cyclopentan-1-ol,
2-(7-carboxyheptyl)-3-(3-hydroxyhept-1-enyl)cyclopentan-1-ol,
2-(7-carboxyheptyl)-3-(3-hydroxyoct-1-enyl)cyclopentan-1-ol,
2-(7-carboxyheptyl)-3-(3-hydroxynon-1-enyl)cyclopentan-1-ol, and
2-(7-carboxyheptyl)-3-(3-hydroxydec-1-enyl)cyclopentan-1-ol, respectively.

Again in the same manner, but using as starting materials, the methyl, ethyl, propyl, isopropyl, n-butyl, n-pentyl or n-hexyl esters of
2-(5-carboxypent-2-enyl)-3-(3-oxopent-1-enyl)cyclopentan-1-one,
2-(5-carboxypent-2-enyl)-3-(3-oxohex-1-enyl)cyclopentan-1-one,
2-(5-carboxypent-2-enyl)-3-(3-oxohept-1-enyl)cyclopentan-1-one,
2-(5-carboxypent-2-enyl)-3-(3-oxooct-1-enyl)cyclopentan-1-one,
2-(5-carboxypent-2-enyl)-3-(3-oxonon-1-enyl)cyclopentan-1-one, and
2-(-carboxypent-2-enyl)-3-(3-oxodec-1-enyl)cyclopentan-1-one, there are obtained the methyl, ethyl, proyl, isopropyl, n-butyl, n-pentyl, and n-hexyl esters of
2-(5-carboxypent-2-enyl)-3-(3-hydroxypent-1-enyl)cyclopentan-1-ol,
2-(5-carboxypent-2-enyl)-3-(3-hydroxyhex-1-enyl)cyclopentan-1-ol,
2-(5-carboxypent-2-enyl)-3-hydroxyhept-1-enyl)cyclopentan-1-ol,
2-(5-carboxypent-2-enyl)-3-(3hydroxyoct-1-enyl)cyclopentan-1-ol,
2-(5-carboxypent-2-enyl)-3-(3-hydroxynon-1-enyl)cyclopentan-1-ol, and
2-(5-carboxypent-2-enyl)-3-(3-hydroxydec-1-enyl)cyclopentan-1-ol, respectively.

Again in the same manner, but using as starting materials, the methyl, ethyl, propyl, isopropyl, n-butyl, n-pentyl or n-hexyl esters of
2-(6-carboxyhex-2-enyl)-3-(3-oxopent-1-enyl)cyclopentan-1-one,
2-(6-carboxyhex-2-enyl)-3-(3-oxohex-1-enyl)cyclopentan-1-one,
2-(6-carboxyhex-2-enyl)-3-(3-oxohept-1-enyl)cyclopentan-1-one,
2-(6-carboxyhex-2-enyl)-3-(3-oxooct-1-enyl)cyclopentan-1-one,
2-(6-carboxyhex-2-enyl)-3-(3-oxonon-1-enyl)cyclopentan-1-one, and
2-(6-carboxyhex-2-enyl)-3-(3-oxodec-1-enyl)cyclopentan-1-one, there are obtained the methyl, ethyl, propyl, isopropyl, n-butyl, n-pentyl, nd n-hexyl esters of
2-(6-carboxyhex-2-enyl)-3-(3-hydroxypent-1-enyl)cyclopentan-1-ol,
2-(6-carboxyhex-2-enyl)-3-(3-hydroxyhex-1-enyl)cyclopentan-1-ol,
2-(6-carboxyhex-2-enyl)-3-(3-hydroxyhept-1-enyl)cyclopentan-1-ol,
2-(6-carboxyhex-2-enyl)-3-(3-hydroxyoct-1-enyl)cyclopentan-1-ol,
2-(6-carboxyhex-2-enyl)-3-(3-hydroxynon-1-enyl)cyclopentan-1-ol, and
2-(6-carboxyhex-2-enyl)-3-(3-hydroxydec-1-enyl)cyclopentan-1-ol, respectively.

Again in the same manner, but using as starting materials, the methyl, ethyl, propyl, isopropyl, n-butyl, n-pentyl or n-hexyl esters of
2-(7-carboxyhept-2-enyl)-3-(3-oxopent-1-enyl)cyclopentan-1-one,
2-(7-carboxyhept-2-enyl)-3-(3-oxohex-1-enyl)cyclopentan-1-one,
2-(7-carboxyhept-2-enyl)-3-(3-oxohept-1-enyl)cyclopentan-1-one,
2-(7-carboxyhept-2-enyl)-3-(3-oxooct-1-enyl)cyclopentan-1-one,
2-(7-carboxyhept-2-enyl)-3-(3-oxonon-1-enyl)cyclopentan-1-one, and
2-(7-carboxyhept-2-enyl)-3-(3-oxodec-1-enyl)cyclopentan-1-one, there are obtained the methyl, ethyl, propyl, isopropyl, n-butyl, n-pentyl, and n-hexyl esters of
2-(7-carboxyhept-2-enyl)-3(3-hydroxypent-1-enyl)cyclopentan-1-ol,
2-(7-carboxyhept-2-enyl)-3-(3-hydroxyhex-1-enyl)cyclopentan-1-ol,
2-(7-carboxyhept-2-enyl)-3-(3-hydroxyhept-1-enyl)cyclopentan-1-ol,
2-(7-carboxyhept-2-enyl)-3-(3-hydroxyoct-1-enyl)cyclopentan-1-ol,
2-(7-carboxyhept-2-enyl)-3-(3-hydroxynon-1-enyl)cyclopentan-1-ol, and
2-(7-carboxyhept-2-enyl)-3-(3-hydroxydec-1-enyl)cyclopentan-1-ol, respectively.

Again in the same manner, but using as starting materials, the methyl, ethyl, propyl, isopropyl, n-butyl n-pentyl or n-hexyl esters of
2-(5-carboxypent-2-ynyl)-3-(3-oxopent-1-enyl)cyclopentan-1-one,
2-(5-carboxypent-2-ynyl)-3-(3-oxohex-1-enyl)cyclopentan-1-one,
2-(5-carboxypent-2-ynyl)-3-(3-oxohept-1-enyl)cyclopentan-1-one,
2-(5-carboxypent-2-ynyl)-3-3-(3-oxooct-1-enyl)cyclopentan-1-one,
2-(5-carboxypent-2-ynyl)-3-(3-oxonon-1-enyl)cyclopentan-1-one, and
2-(5-carboxypent-2-ynyl)-3-(3-oxodec-1-enyl)cyclopentan-1-one, there are obtained the methyl, ethyl, propyl, isopropyl, n-butyl, n-pentyl or n-hexyl esters of
2-(5-carboxypent-2-ynyl)-3-(3-hydroxypent-1-enyl)cyclopentan-1-ol,
2-(5-carboxypent-2-ynyl)-3-(3-hydroxyhex-1-enyl)cyclopentan-1-ol,
2-(5-carboxypent-2-ynyl)-3-(3-hydroxyhept-1-enyl)cyclopentan-1-ol,
2-(5-carboxypent-2-ynyl)-3-(3-hydroxyoct-1-enyl)cyclopentan-1-ol, 2-(5-carboxypent-2-ynyl)-3-(3-hydroxynon-1-enyl)cyclopentan-1-ol, and 2-(5-carboxypent-2-ynyl)-3-(3-hydroxydec-1-enyl)cyclopentan-1-ol, respectively.

Again in the same manner, but using as starting materials, the methyl, ethyl, propyl, isopropyl, n-butyl, n-pentyl or n-hexyl esters of 2-(6-carboxyhex-2-ynyl)-3-(3-oxopent-1-enyl)cyclopentan-1-one, 2-(6-carboxyhex-2-ynyl)-3-(3-oxohex-1-enyl)cyclopentan-1-one, 2-(6-carboxyhex-2-ynyl)-3-(3-oxohept-1-enyl)cyclopentan-1-one, 2-(6-carboxyhex-2-ynyl)-3-(3-oxooct-1-enyl)cyclopentan-1-one, 2-(6-carboxyhex-2-ynyl)-3-(3-oxonon-1-enyl)cyclopentan-1-one, and 2-(6-carboxyhex-2-ynyl)-3-(3-oxodec-1-enyl)cyclopentan-1-one, there are obtained the methyl, ethyl, propyl, isopropyl, n-butyl, n-pentyl, and n-hexyl esters of 2-(6-carboxyhex-2-ynyl)-3-(3-hydroxypent- b-enyl)cyclopentan-1-ol, 2-(6-carboxyhex-2-ynyl)-3-(3-hydroxyhex-1-enyl)cyclopentan-1-ol, 2-(6-carboxyhex-2-ynyl)-3-(3-hydroxyhept-1-enyl)cyclopentan-1-ol, 2-(6-carboxyhex-2-ynyl)-3-(3-hydroxyoct-1enyl)cyclopentan-1-ol, 2-(6-carboxyhex-2-ynyl)-3-(3-hydroxynon-1-enyl)cyclopentan-1-ol, and 2-(6-carboxyhex-2-ynyl)-3-(3-hydroxydec-1-enyl)cyclopentan-1-ol, respectively.

Again in the same manner, but using as starting materials, the methyl, ethyl, propyl, isopropyl, n-butyl, n-pentyl or n-hexyl esters of 2-(7-carboxyhept-2-ynyl)-3-(3-oxopent-1-enyl)cyclopentan-1-one, 2-(7-carboxyhept-2-ynyl)-3-(3-oxohex-1-enyl)cyclopentan-1one, 2(7carboxyhept-2-ynyl)-3-(3-oxohept-1-enyl)cyclopentan-1-one, 2-(7-carboxyhept-2ynyl)-3-(3-oxooct-1-enyl)cyclopentan-1-one, 2-(7-carboxyhept-2-ynyl)-3-(3oxonon-1enyl)cyclopentan-1one, and 2(7-carboxyhept-2-ynyl)-3-(3-oxodec-1-enyl)cyclopentan1-one, thereare obtained the methyl, ethyl, propyl, isopropyl, n-butyl, n-pentyl, and n-hexyl esters of 2-(7-carboxyhept-2-ynyl)-3-(3-hydroxypent-1-enyl)cyclopentan-1-ol, 2-(7-carboxyhept-2-ynyl)-3-(3-hydroxyhex-1enyl)cyclopentan-1-ol, 2-(7-carboxyhept-2-ynyl)-3-(3-hydroxyhept-1enyl)cyclopentan-1-ol, 2-(7-carboxyhept-2-ynyl)-3-(3-hydroxyoct-1-enyl)cyclopentan-1-ol, 2-(7-carboxyhept-2-ynyl)-3-(3-hydroxynon-1-enyl)cyclopentan-1-ol, and 2-(7-carboxyhept-2-ynyl)-3-(3-hydroxydec-1enyl)cyclopentan-1-ol, respectively.

2-(6-Carboxyhex-2-enyl)-3-(3-hydroxyoct-1-enyl)cyclopentan-1-ol methyl ester has $\gamma_{max}^{Film}$ 3500 and 1735 cm$^{-1}$ and its corresponding acid, 2-(6-carboxyhex-2-enyl-3-(3-hydroxyoct-1-enyl)cyclopentan-1-ol has $\gamma_{max}^{Film}$ 3600 — 3200 (broad) and 1710 cm$^{-1}$.

2-(6-Carboxyhex-2-ynyl)-3-(3-hydroxyoct-1-enyl)cyclopentan-1-ol methyl ester has $\gamma_{max}^{Film}$ 3500 and 1735 cm$^{-1}$ and its corresponding acid, 2-(6-carboxyhex-2-ynyl)-3-(3-hydroxyoct-1-enyl)cyclopentan-1-ol has $\gamma_{max}^{Film}$ 3600 — 3200 (broad) and 1710 cm$^{-1}$.

Note also that by following the procedure of Example 18 to prepare the 1-tetrahydropyranyl ether of 2-(6-carboxyhex-2-enyl)-3-(3-hydroxyoct-1-enyl)cyclopentan-1-ol methyl ester, followed by acid hydrolysis of the resulting tetrahydropyranyl ether according to the conditions of British Pat. No. 1,218,988, the tetrahydropyranyl ethers of formula XII, described herein in Example 10, may be converted to the respective compounds of formula VIIIa, described herein in the present example.

We claim:

1. A compound of the formula VIIIa

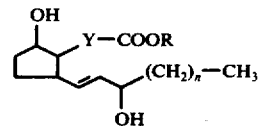

in which R is hydrogen or lower alkyl, n is an integer from 1 to 6 and Y is CH$_2$—(a)—(CH$_2$)$_m$ wherein (a) is C≡C and $m$ is an integer from 2 to 4.

2. 2-(6-Carboxyhex-2-ynyl)-3-(3-hydroxyoct-1-enyl)-cyclopentan-1-ol methyl ester, as claimed in claim 1.

3. 2-(6Carboxyhex-2-ynyl)-3-(3-hydroxyoct-1-enyl)-cyclopentan-1-ol, as claimed in claim 1.

* * * * *